United States Patent
Szasz et al.

(10) Patent No.: US 9,320,911 B2
(45) Date of Patent: Apr. 26, 2016

(54) RADIOFREQUENCY HYPERTHERMIA DEVICE WITH TARGET FEEDBACK SIGNAL MODULATION

(75) Inventors: Andras Szasz, Páty (HU); Oliver Szasz, Páty (HU); Nora Iluri, Weston, MA (US)

(73) Assignee: Oncotherm Kft., Páty (HU)

( * ) Notice: Subject to any disclaimer, the term of this patent is extended or adjusted under 35 U.S.C. 154(b) by 1390 days.

(21) Appl. No.: 13/123,838

(22) PCT Filed: Oct. 13, 2009

(86) PCT No.: PCT/EP2009/007342
§ 371 (c)(1),
(2), (4) Date: Nov. 17, 2011

(87) PCT Pub. No.: WO2010/043372
PCT Pub. Date: Apr. 22, 2010

(65) Prior Publication Data
US 2012/0065714 A1    Mar. 15, 2012

(51) Int. Cl.
*A61N 1/40* (2006.01)
*A61F 7/12* (2006.01)
*A61B 18/12* (2006.01)
*A61B 18/00* (2006.01)

(52) U.S. Cl.
CPC ............ *A61N 1/403* (2013.01); *A61B 18/1206* (2013.01); *A61B 2018/00702* (2013.01); *A61B 2018/00785* (2013.01)

(58) Field of Classification Search
CPC combination set(s) only.
See application file for complete search history.

(56) References Cited

U.S. PATENT DOCUMENTS

2004/0230263 A1    11/2004  Samulski
2005/0015125 A1 *   1/2005  Mioduski et al. ............. 607/102

FOREIGN PATENT DOCUMENTS

EP       1 916 013          4/2008
RU       2242256        * 12/2004

OTHER PUBLICATIONS

Machine Translation of RU 2242256.*
Oncotherm—Using EHY 2000, Apr. 30, 2008.
Oncotherm—EHY 2000 Series, Hightech Medicine, Apr. 21, 2008.
Oncotherm—Oncothermia Concept and Practice, Nov. 21, 2007.
Szasz "Electromagnetic hyperthermia procedure: the capacitive coupling" www.oncotherm.hu/images/Public/Kapazitive%20kopplung%202003.pdf, 2003.
Oncotherm—Rife and Hyperthermia, 2007.

* cited by examiner

*Primary Examiner* — Joseph Stoklosa
*Assistant Examiner* — Adam Avigan
(74) *Attorney, Agent, or Firm* — Meyertons, Hood, Kivlin, Kowert & Goetzel, P.C.; Eric B. Meyertons

(57) ABSTRACT

The present invention relates to a radiofrequency (RF) hyperthermia device for capacitive coupling comprising a radiofrequency source, an amplifier, a sensor, a feedback amplifier and a modulation signal generator, wherein the radiofrequency source produces a source signal which is modulated by the modulation signal generator, amplified by the amplifier and directed to a target, the sensor receives a feed back signal from the target that is directed to the feed back amplifier, wherein the feedback signal is amplified by the feedback amplifier and modulates the source signal to generate a target modified signal. This radiofrequency (RF) hyperthermia device is designed for increasing the selectivity of the hyperthermia treatment.

11 Claims, 13 Drawing Sheets

FIGURES

State of the art

State of the art

RADIOFREQUENCY HYPERTHERMIA DEVICE WITH TARGET FEEDBACK SIGNAL MODULATION

BACKGROUND OF THE INVENTION

1. Field of the Invention

The present invention relates to a radiofrequency (RF) hyperthermia device comprising a radiofrequency source, an amplifier, a sensor, optional a feedback amplifier and a modulation signal generator, wherein the radiofrequency source produces a source signal which is modulated by the modulation signal generator, amplified by the amplifier and directed to a target, the sensor receives a feed back signal from the target that is directed to the feed back amplifier, wherein the feedback signal is amplified if needed by the feedback amplifier and modulates the source signal to generate a target modified signal. This radiofrequency (RF) hyperthermia device is designed for increasing the selectivity of the hyperthermia treatment.

2. Description of the Relevant Art

Heating is widely applied in a many areas of medicine and also used for cosmetic treatments. For example radiofrequency/microwave hyperthermia devices can be used to force energy absorption in tissue to cause damage to unwanted structures and/or increase the temperature of a targeted area above the normal body temperature. One use of hyperthermia devices is the treatment of cancer.

With hyperthermia the problem of selectivity still occurs since it is desired that the target tissue/cell is selectively heated in order to destroy or support destroying the target tissue/cell while the deterioration of healthy tissue should be minimized.

Therefore there is still a need to provide more selective hyperthermia treatments in order to increase efficacy of cancer treatment and the treatment of other diseases.

Thus object of the present invention is to provide a radiofrequency device for selective hyperthermia treatment, especially of cancer and proliferative diseases as well as pain.

This object is solved by the teaching of the independent claims. Further advantageous features and embodiments are evident from the description, the examples and the dependent claims.

SUMMARY OF THE INVENTION

The present invention relates to a radiofrequency hyperthermia device for capacitive coupling and without dipole antenna comprising a radiofrequency source (1), an amplifier (2), a sensor (3) and a modulation signal generator (13) wherein the radiofrequency source produces a source signal (8) which is modulated by the modulation signal generator (13) to generate a modulated source signal (10), the modulated source signal (10) is amplified by the amplifier (2) and directed to a target (17), and the sensor receives a feedback signal (5) from the target, wherein the feedback signal (5) modulates the source signal (8) to generate a target modified modulated signal (4).

In case the feedback signal (5) needs to be amplified, a feedback amplifier (6) for amplifying the feedback signal (5) can be used in the inventive device.

In case the feedback amplifier (6) is present, the present invention relates to a radiofrequency hyperthermia device for capacitive coupling and without dipole antenna comprising a radiofrequency source (1), an amplifier (2), a sensor (3), a feedback amplifier (6) and a modulation signal generator (13), wherein the radiofrequency source produces a source signal (8) which is modulated by the modulation signal generator to generate a modulated source signal (10), the modulated source signal (10) is amplified by the amplifier and directed to a target (17), and the sensor receives a feedback signal (5) from the target that is directed to the feedback amplifier (6), wherein the feedback signal is amplified by the feedback amplifier (6) and modulates the source signal to generate a target modified modulated signal (4).

It is also possible to combine the function of two or more parts of the inventive hyperthermia device. For example, the modulation signal generator (13) and the feedback amplifier (6) can be combined so that amplification and modulation is performed by one part of the device. In such a case the modulation signal generator (13) could also amplify the feedback signal (5) and also modulate the feedback signal (5) in order to generate the modulation signal (12).

The inventive hyperthermia device uses capacitive coupling between the electrodes and RF current which also runs through the target tissue of the patient while the body part of the patient between the electrodes acts like a dielectric material wherein the target tissue is heated by Joule heat ($Q=I^2R$) generated by conversion of the current flow through the target tissue into heat as well as by the potential difference used for an electric field effect. Selectivity of the generation of heat mostly within the target tissue or the diseased tissue and not the healthy tissue is achieved by using conductivity differences of the healthy tissue in regard to the diseased or target tissue. The target tissue such as a malignant tumor tissue has a higher complex or overall conductivity (admittance) than healthy tissue and consequently has a higher absorption rate of the current going through it in comparison to healthy or normal tissue so that the Joule heat is mostly generated when the current passes the target tissue.

A state-of-the-art hyperthermia device is described in US 2004/0230263 A1. It differs, however, from the present invention in the following features: In the device of US 2004/0230263 A1 dipole antennas (radiative coupling) are used. Radiative RF is applied through the patient or more precisely through the target tissue by using absorbed RF radiation. In the radiative solution the target is independent from the circuit, the feedback is made by the standing-wave-ratio (SWR) only, which measures the reflected power in comparison to the forwarded. The device of the present invention does not use dipole antennas; the inventive device uses a condenser arrangement wherein the patient's body between the at least one electrode and at least one counter-electrode is the dielectric material which is part of the conductive circuit. This enables a direct control of the target as a part of the circuit, and generates a more precise and accurate feedback for controlling the process. The present invention uses condenser electrodes (capacitive coupling) for the application of RF-current through the respective body cross section. This conventional device induces phase-shifted interference between the antennas and interference of their standing wave radiation in order to tune the focus on the desired area. The present invention uses conductivity differences of the respective tissues (e.g. malignant tumor tissue has a higher conductivity than healthy tissue), thus leading to an automatic selection of the focus. This has immediate consequences on expansible organs like the lung or the heart, or if the patient moves during a treatment session which may exceed one hour. While the focus in the conventional device remains at the spot on which it was focused before, independent from the actual position of the tumor, the present invention follows any movement of the target because the RF current automatically flows in the correct direction. In this conventional device the target is treated like an electrically independent object absorbing the radiated energy. The present invention uses the target as a part of the electric circuit, as a dielectric material of a condenser in a resonant circuit. Consequently, the heating process is carried out and controlled in a different fashion. This conventional device uses SAR (specific absorption rate) absorbed energy as the only heating mechanism for achieving a beneficial effect. The present invention uses Joule heat ($Q=I^2R$) by converting the current flow into heat as well as the potential difference for an electric field effect. This conventional device controls temperature only as a tool for reproducing and standardising the therapy. In contrast, the present invention uses the absorbed energy (J/kg) and the conductivity of the patient ($S=1/R$) for strict control of the therapy conditions. This conventional device implicitly assumes that the success of the therapy depends only on the heat effect relative to the achieved temperature. By such a method mainly necrosis is caused in the target tissue. The present invention, however, does not require achieving such high temperatures at which necrosis occurs because the field effect causes apoptosis at lower temperatures. Thus the inventive device treats tumorous or malignant tissue, cancer, tumours and especially solid tumours by inducing and/or causing apoptosis while common devices using radiative coupling induce necrosis. The device of the present invention does not use radiative coupling and uses the patient and especially the tissue of the patient between the electrodes wherein said tissue comprises the diseased tissue or also called the target tissue as dielectric material or dielectricum as part of the electric circuit.

Since US 2004/0230263 A1 is regarded as closest prior art, we summarize the above discussed differences in regard to the present invention. The statement made in regard to the arrangement of the single parts of the hyperthermia device or the technical parameters of the inventive device in comparison to US 2004/0230263 A1 are of course general statements and are always true and valid and not only in regard to US 2004/0230263 A1.

1. US 2004/0230263 A1 is based on the RF-radiation/absorption processes, not at all on the RF current conduction like the present invention.
2. The multiple antenna solution of US 2004/0230263 A1 focuses the energy on the target by the phase-array method which means that their amplitude and phase is individually adjusted for proper focusing. In our case it is completely different. The focus is made automatically by the conduction differences of the malignant target and the surrounding healthy tissues, no focusing adjustment, no multiple antennas and no radiation fitting is used as the device of the present invention does.
3. The proper focusing in US 2004/0230263 A1 case requires high frequency, (130-160 MHz, about one order of magnitude higher than the frequency the inventive hyperthermia device uses, which uses preferably a fix carrier frequency of 13.56 MHz).
4. The frequency in US 2004/0230263 A1 is not a carrier of the modulation; the modulation disclosed in US 2004/0230263 A1 is applied to differentiate the various radiation antennas. US 2004/0230263 A1 uses phase modulation (phase shifters). In the present invention a single resonant circuit carries the amplitude modulated signal, no phase modulation is used in the present inventive device.
5. In US 2004/0230263 A1 the feedback is the standing-wave ratio fit and that causes an optimal radiated energy-coupling. In the present invention the feed-back is the forwarded energy, and a capacitive coupling is applied.
6. US 2004/0230263 A1 has to change the frequency for the best fit, in order to obtain a proper phase array adjustment. In the present invention the frequency is strictly frozen.
7. US 2004/0230263 A1 uses frequencies which are not allowed for free applications in hospitals, so a Faraday-cage is necessary for legal use. In the inventive hyperthermia device the fixed legal frequency allows for a legal application, without expensive, dangerous and complicated extra shielding. In the frequency range which is used by the device of US 2004/0230263 A1 there is no such interval, which could be used freely without Faraday-cage. Anyway, the free frequencies used by the device of the present invention are fixed narrow ranges, which do not allow frequency sweep for tuning.
8. The frequency used by the inventive device is low and does not exceed 50 MHz. In contrast, the radiation solution has to use a high frequency of at least 100 MHz, otherwise accurate focusing is impossible. Generally, the antenna (radiative) has to be optimized to 50 Ohm (this is the accepted standard). This function is made by the tuner. In the present invention the SWR is important only for the electronical protection of the amplifier (if it goes far from 50 Ohm, it could be destroyed by the reflected power). In the present invention the low frequency of preferably 13.56 MHz or 6.78 MHz or 27.12 MHz or 40.68 MHz or any value inbetween enables the inventive device to suppress radiation and gain conduction only.
9. The main difference in the construction of the devices of US 2004/0230263 A1 and of the present invention is in the antenna solution of US 2004/0230263 A1 which is drastically different from the construction of the inventive device. The device of US 2004/0230263 A1 must have Hertz-dipoles to radiate, while the inventive device does not have and does not need such dipole antennas. US 2004/0230263 A1 needs a circular applicator for focusing, the inventive device needs directional current and not circular radiation.
10. The device of US 2004/0230263 A1 has an antenna-set which contains multiple-dipoles (many dipole antennas are necessary around the body) while the inventive device consists of a condenser arrangement (it is a capacitive coupling, and not an antenna) comprising an electrode and a counter electrode.
11. US 2004/0230263 A1 modulates the phase between the antennas to obtain the best focus (in fact diffraction coherence, interference) on the target area, while the present invention uses and is designed for amplitude modulation.
12. The device according to US 2004/0230263 A1 needs somehow an independent identification of the focus (temperature measurement by invasive way or by MRI imaging, which is rather expensive) otherwise it is not clear where the heat treatment shall be focused. The feedback signal in US 2004/0230263 A1 reflects only the focus sharpness and they can target any area by phase modulation, but they need an idea where they are, in order to focus the treatment. For the present invention no such knowledge is necessary. It is only important to make sure that the RF-current flows through the target area and this is easily achieved as long as the target area is between the electrodes, i.e. the electrode and the counter electrode. The SWR of course changes if the patient moves (or has physiological movements like breathing or heart-beats, or digesting movements of stomach of intestines, etc.). In the present invention the movement (which leaves the target area between the electrode and counter electrode) does not have any role or negative influence, the current automatically follows the movements through conductivity.
13. The modulation according to US 2004/0230263 A1 is defined by the geometry of the tissue (tumor location and size), so it is a part of the focus. In the present invention the modulation has no effect on the focus, it is effective on a cell-killing mechanism, forcing apoptosis, instead of necrosis caused by high temperature.

14. In the present invention, the modulation has a pattern which causes the therapeutic effect, and which could also be switched off, when only heating is necessary in the targeted area. The modulation according to US 2004/0230263 A1 must be running permanently, otherwise the focus will be lost.

The hyperthermia device of the present invention is especially useful for the treatment and after-treatment of tumours, cancer, metastases and carcinomas as well as pain and diseases of the central nervous system.

The treatment, after-treatment and/or prophylaxis of pain or the medical indication pain comprises pain caused by cancer, tumor associated pains, chronic pain and chronic pain conditions, head pains, migraine, migraine headache, neuralgias, trigeminal neuralgia, post-therapeutic neuralgia, neuropathic pains, persistent musculoskeletal pains and persistent visceral pains.

The indications persistent musculoskeletal pains and persistent visceral pains further comprise persistent back pains, persistent neck pains, persistent shoulder pains, persistent joint pains and fibromyalgia.

The pain which can be treated by the present inventive device can be caused and/or associated with cancer, tumors, the premenstrual syndrome, mastalgia, stomach pain associated with irritable colon and pains associated with carcinoid syndrome.

If a pain event lasts for more than three to six months, it is referred to as chronic pain. Causes thereof may be incurable diseases such as malignant tumors or rheumatic diseases. However, the connection between the pain and the disorder or respectively the disease which originally caused the pain is often no longer identifiable or the original disorder can no longer be remedied. Furthermore, various environmental influences like stress or weather changes can trigger or enhance the pain. A chronic manifestation of pain often includes different forms of pain.

Back pains (amongst others as a consequence of herniated discs, nerve root compression syndrome), head pains (amongst others migraine, tension-type headache, cluster headache), rheumatic pains (amongst others arthritis, fibromyalgia), neuralgias (amongst others trigeminal neuralgia, herpes zoster-induced pain), tumor associated pains (amongst others brain tumor, bone metastases), degenerative pains (amongst others osteoporosis, arthrosis) and phantom pains (amongst others after amputation, plexus lesion) are mentioned as the most frequent forms of chronic pain.

Chronic pain often last for several years or decades. Frequently, patients suffering from chronic pain develop emotional problems. Many pain patients suffer from inactivity and listlessness; they feel hopeless and desperate, complain about feelings of anxiety and depression, perceive themselves as limited in their self-esteem. Such psychic symptoms are warning signals of a chronification, just as general, nonspecific physical complaints such as intestine associated problems (diarrhea or respectively constipation), irritable bladder, dizziness, dyspnea, palpitations or a feeling of tightness in the chest.

Different mechanisms in the peripheral and central nervous systems are involved in the causation of chronic pain. The sensitization of pain fibers and their local hyperexcitability are substantial pathogenic mechanisms which are relevant as far as peripheral pain perception in the course of the causation of chronic pain conditions is concerned. Other pathomechanisms comprise the longer lasting enhancement of pain signals and a recruitment of usually silent nerve fibers in the area of the spinal cord that lead to a larger spatial extension of the pain perception. Finally, in the brain the pain potentials arriving in increased number from the periphery lead to changes in signal transmission in terms of an enhancement of the pain perception and a long-term change in pain processing.

Even when lasting only for a few minutes, intensive pain stimuli can lead to persistent structural and functional changes which intensify the transmission and the processing of pain stimuli. These procedures are similar to cellular activities such as those that can be observed in all more complex, neuronal learning processes; consequently, it is analogously referred to as pain memory. In said context, the term pain memory includes the ability of the nervous system to generate a memory trace for an occurred painful stimulation through the whole pain processing system.

We have several reports from 48 patients having pain describing how their pain disappeared during hyperthermia treatment. These patients suffered from pain associated with tumors, rheumatic pain, migraine, joint-pains or other kinds of pain. Example 5 and FIG. 27 disclose the change in pain before and after the hyperthermia treatment and FIG. 27 clearly shows the beneficial effects of hyperthermia treatment. About 16 patients with severe paid and 8 patients with moderate pain did not feel any pain at all after the treatment and 5 patients with severe pain stated a vehement reduction of pain after the treatment and the remaining patient stated to feel no remarkable difference in the degree of pain.

Thus one third of all patients were pain free after the treatment which demonstrated the preferred use of the inventive hyperthermia device for treatment of any kind of pain.

Oncothermia

Oncothermia is becoming ever the more an established method in tumor therapy. By using conventional oncothermia (without the modulation method and device of the present invention) a number of retrospective clinical studies prove an oncothermia effect in humans. Treatment of metastatic liver tumors is very complex because of an effective cooling of the voluminous blood flow and the sensitivity of the organ due to chemotoxicity from previous treatments. Oncothermia application to this organ delivered very positive results. Colorectal liver metastases were the topic of four different studies (Hager E D et al (1999) Deep hyperthermia with radiofrequencies in patients with liver metastases from colorectal cancer. Anticancer Res. 19(4C):3403-3408). The sensitivity of the liver due to chemotherapy in advanced cases (when other chemo-treatments proved to be unsuccessful) is well observable for the combined treatment compared to oncothermia monotherapy. The device of the present invention is especially useful for the treatment of metastatic liver tumors and colorectal liver metastases.

The pancreas carcinoma is a rapid and aggressive disease, and not too many conventional hyperthermia results can be found in this location. Oncothermia results presented on ASCO, and other conferences are significantly improving the achievements of conventional treatment methods. Results were repeated in six different clinics in two countries, thus the gain is based on statistical evidence. However, we were again able to show the beneficial effect of the device of the present invention in treating pancreas carcinoma so that another preferred use of the inventive device is the treatment and after-treatment of pancreas carcinoma.

The lung is also a complicated organ for hyperthermia because of the permanent cooling-ventilation of breathing. Oncothermia, due to a non-equilibrium approach, is an excellent treatment for that as well. Also remarkable effects were achieved by the use of the inventive hyperthermia device (see example 6). Thus the inventive device is also highly useful for the treatment of lung cancer.

As disclosed above in detail, the hyperthermia device of the present invention is also highly useful for the treatment and prophylaxis of various kinds of pains (see example 5).

Disorders of the central nervous system (tumors or other disorders in brain and/or spinal cord) are also treatable. The safe treatment could be demonstrated by spectacularly documented near-eye cases, when the tumor disappeared by oncothermia treatment, while the eye remained unhurt, intact after treatment (see example 7).

The pain management both by heat and field (TENS="transcutane electric nerve stimulation", TENB="transcutane electric nerve block") is also effective, due to the applied transcutane electric field, which is a standard practice of this treatment.

The differences between the common hyperthermia devices and the hyperthermia device of the present invention as well as the common hyperthermia treatment and the oncothermia treatment by means of the hyperthermia device of the present invention are as follows:

1. Common RADIATIVE HYPERTHERMIA operates with the temperature alone, (classical Hypocrite's idea). CONDUCTIVE HYPERTHERMIA used by the inventive device uses the electric field in synergy with heat-energy (modern bio-physical concept). [Note: temperature and heat are definitive different quantities. Temperature is not a quantity, not proportional to mass or volume. Temperature characterizes the equilibrium only. Heat is active energy, which partly increases the temperature, partly modifies chemical bonds and molecular structures, which is the aim of the present inventive device. For example, we are eating (absorbing energy from the food measured in kj) not for increasing our body temperature. The fact that heat is also measured in kj does not indicate identical physical parameters.]
2. Common RADIATIVE HYPERTHERMIA operates by simple energy absorption; the patient is independent from the electronic device. In a CONDUCTIVE HYPERTHERMIA system like the inventive device the patient is part of the electric circuit (condenser) like a dielectric material. This allows a tight and strict control. [Note: remember: that the patient control is crucial, so RADIATIVE HYPERTHERMIA needs MRI during treatment, CONDUCTIVE HYPERTHERMIA does not request such sophistication.]
3. Common RADIATIVE HYPERTHERMIA uses short wavelength, high frequency [70 MHz-2400 MHz]. CONDUCTIVE HYPERTHERMIA uses 13.56 MHz, at least five times lower. [Note: the penetration depth of the electromagnetic waves into the body is inversely and sharply depends on the frequency. CONDUCTIVE HYPERTHERMIA penetration is around 20 cm, RADIATIVE HYPERTHERMIA (depending in its actual frequency) does not reach one quarter of it on the same patient conditions.]
4. Common RADIATIVE HYPERTHERMIA uses artificial focusing, for what very sophisticated software and hardware is necessary. CONDUCTIVE HYPERTHERMIA has a self-selective (self-focusing) facility by the RF-conduction selection. [Note: the cancer tissue has higher conductivity than the healthy one, so the RF-current which is used by CONDUCTIVE HYPERTHERMIA automatically chooses that way.]
5. By the movements of the patients (e.g. breathing) RADIATIVE HYPERTHERMIA has no correction of its focus, so the danger of the misfocusing or the larger one than necessary is exists. CONDUCTIVE HYPERTHERMIA corrects it automatically by the above self-selection.
6. Common RADIATIVE HYPERTHERMIA has to have a complex preparation of the patient and very sophisticated handling. CONDUCTIVE HYPERTHERMIA is simple, easy to use, cost-effective.

DESCRIPTION OF THE FIGURES

Advantages of the present invention will become apparent to those skilled in the art with the benefit of the following detailed description of embodiments and upon reference to the accompanying drawings in which:

FIGS. 14 (A and B)

FIGS. 17 (A and B) refer to the Demodulation, a process with a particular threshold-noise relation. (Either the threshold changed with a fixed noise amplitude, or the noise amplitude changes with a fixed sensitivity threshold).

Figure 1:
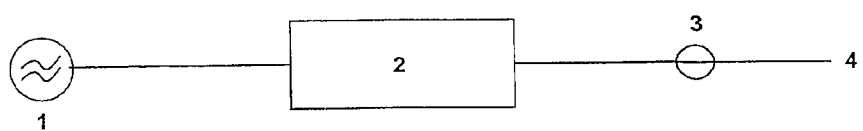
FIG. 1 shows a state of the art radiofrequency device.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DESCRIPTION OF THE INVENTION

The present invention is directed to a radiofrequency hyperthermia device for capacitive coupling with conductive electrodes, forcing RF-current between them and without dipole antenna comprising a radiofrequency source (1), an amplifier (2), a sensor (3), optionally a feedback amplifier (6) and a modulation signal generator (13) wherein the radiofrequency source produces a source signal (8) which is modulated by the modulation signal generator (13) to generate a modulated source signal (10), the modulated source signal (10) is amplified by the amplifier (2) and directed to a target (17), and the sensor receives a feedback signal (5) from the target that is directed to the feedback amplifier (6) if present, wherein the feedback signal (5) is amplified by the feedback amplifier (6), if amplifying is necessary and the feedback signal (5) modulates the source signal (8) to generate a target modified modulated signal (4). Thus, the essential parts of the device are the radiofrequency source (1), the amplifier (2), the sensor (3), and the modulation signal generator (13). Moreover preferred is also the presence of a feedback amplifier (6), but this is not mandatory. All further parts are optional and not necessarily required but for certain embodiments preferred.

The inventive device will be described with reference to FIGS. 1 to 7. The numbering of the parts of the inventive device in the Figures is as follows.

Figure 6:
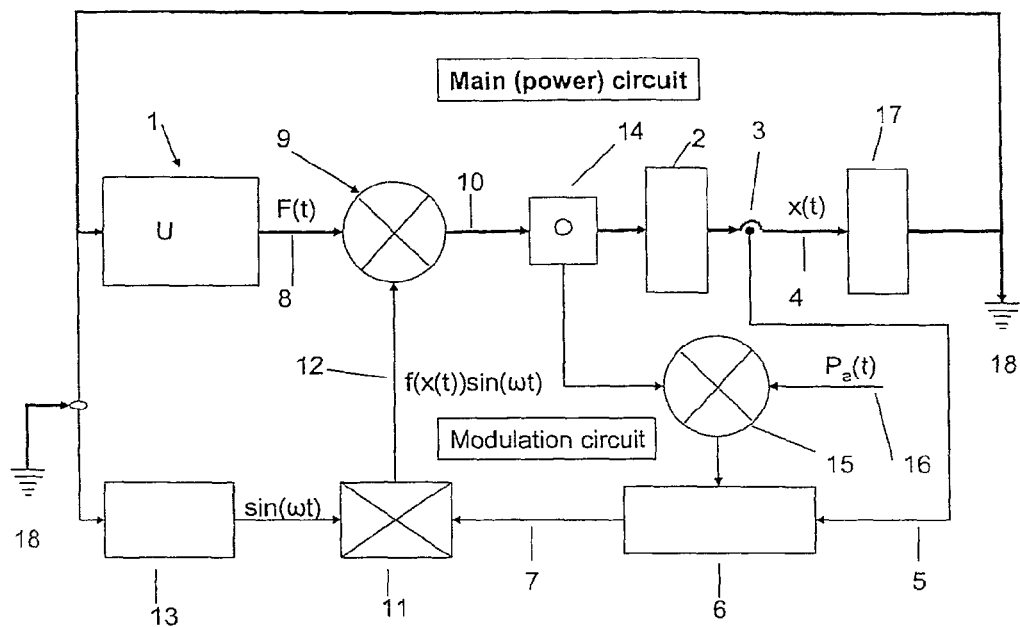
FIG. 6 shows a detailed embodiment of the present invention as shown in FIG. 5 with a feedback sensor at a first position (1)
Figure 7:
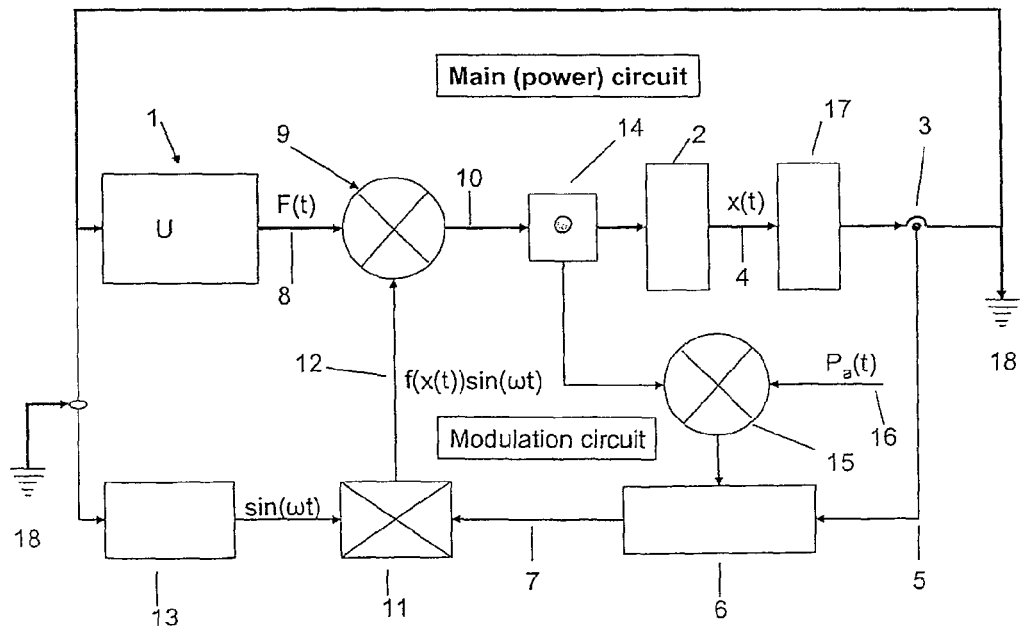
FIG. 7 shows a detailed embodiment of the present invention as shown in FIG. 5 with a feedback sensor at a second position (2)
Figure 13:
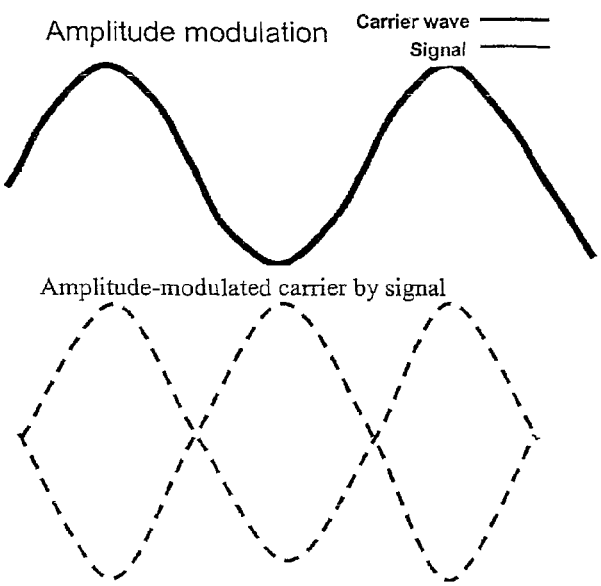
FIG. 13 shows an example for a modulated signal.

(1): a signal generator (oscillator—the radiofrequency source) which provides the selected frequency (preferably 13.56 MHz) by means of a fixed stable quartz-oscillator, (2): an amplifier (RF) which provides the necessary energy supply for the conduction heating wherein the tuner optimizes the conduction for the individual patient, (3): a feedback sensor (current/power) signal sampling unit (RF-current sensor) which controls the forwarded power of the source and the reflected power of the target, (4): an x(t)—amplified and target-modified signal (modulated signal) which is responsible for the treatment in the target tissue, (5): a feedback signal which carries the information of the actual treatment in a complex form and contributes to its control, (6): a feedback amplifier which amplifies the feedback signal up to the desired level for further use, (7): In FIGS. 6 and 7: an amplified feedback signal, corresponding to (5) in FIGS. 1-5, (8): a F(t)—carrier signal which is the power RF-signal (preferably at 13.56 MHz) corresponding to the amplitude modulated by the modulator (9), (9): a modulator which effects the changes in amplitude, (10): a modulated signal which could look like shown in FIG. 13, (11): a multiplicator (feedback correction to the modulation) which fits the modulation to the respective feedback, (12): a modulation signal which represents the "information" carried by the carrier wave (preferably at 13.56 MHz), (13): a modulation signal-generator (e.g. pink noise generator) provides the modulation signal; in FIG. 5 a modulation signal-generator (13) (e.g. pink noise generator) is present as one essential part of the inventive device, (14): optionally, a signal checking unit (power/current sensor) which senses the signal-amplitude for control purposes, (15): optionally, a comparator to a reference signal ($P_a(t)$) which controls the signal by comparison to the reference, (16): optionally, a reference signal ($P_a(t)$), as a stable signal for fixing signal levels, (17): a load (the target tissue to be treated), in general the patient, and (18): a RF-ground, a ground level not necessarily identical with the general ground (earth-potential). This ground is modified by the respective potential distribution of the RF signal as a function of its wavelength.

Figure 2:
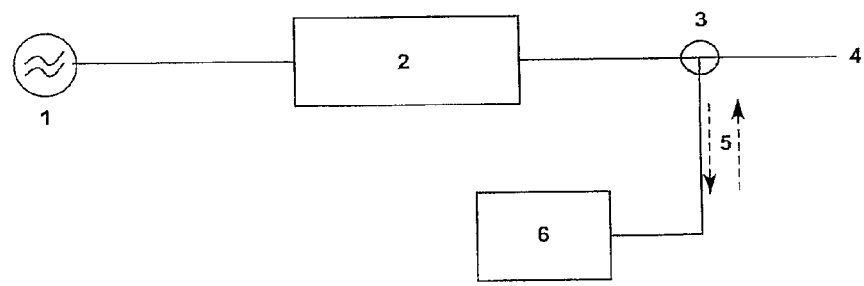
FIG. 2 shows a state of the art radiofrequency device with multiple parallel channels which can be adjusted for modulation without feedback from the target tissue.

In a conventional state of the art system, as shown in FIGS. 1 and 2, the sensor (3) is only used to measure the strength of the signal (8) being directed to the target from the signal source (1), but no modulation feedback and/or no amplitude modulation is applied. A modulation could be applied at the outgoing signal by the sensor (3), but in this case the modulation point is after the amplifying point and no feedback of the modulation can be applied.

Figure 5:
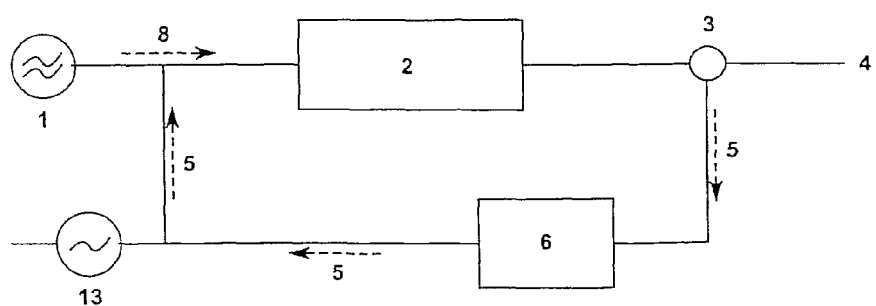
FIG. 5 shows an embodiment of the present invention with pink noise generator as modulation signal generator (13) and a feedback amplifier (6)

FIG. 5 provides a simplified view of the inventive device. The following description of the operation of the inventive device is based on the block diagram of the operation of the device provided in FIGS. 6 and 7. FIGS. 6 and 7 show both the main (power) circuit required for any hyperthermia treatment, including conventional hyperthermia treatment, and the additional modulation circuit(s) required by the inventive device.

The present invention relates to a radiofrequency (RF) hyperthermia device comprising a radiofrequency source (1), an amplifier (2), a sensor (3), a feedback amplifier (6) and a modulation signal generator (13), but does not comprise one or more dipole antennas, wherein the radiofrequency source (1) produces a source signal (8) which is modulated by the modulation signal generator (13) to generate a modulated source signal (10), the modulated source signal (10) is amplified by the amplifier (2) and directed to a target (17), the sensor (3) receives a feed back signal (5) from the target (17) that is directed to the feed back amplifier (6), wherein the feedback signal (5) is amplified by the feedback amplifier (6) and modulates the source signal (8) to generate a target modified modulated source signal (4). This radiofrequency (RF) hyperthermia device is designed for increasing the selectivity of the hyperthermia treatment. Also in this embodiment the presence of the feedback amplifier (6) is preferred but not necessarily required if the feedback signal is strong enough and does not need to be amplified.

In case the feedback amplifier (6) is not necessarily required or in case the feedback amplifier (6) in integrated into the modulation signal generator (13), the inventive RF hyperthermia device using capacitive coupling comprises a radiofrequency source (1), an amplifier (2), a sensor (3) and a modulation signal generator (13) probably with integrated amplifier function, but does not comprise one or more dipole antennas, wherein the radiofrequency source (1) produces a source signal (8) which is modulated by the modulation signal generator (13) to generate a modulated source signal (10), the modulated source signal (10) is amplified by the amplifier (2) and directed to a target (17), the sensor (3) receives a feedback signal (5) from the target (17), wherein the feedback signal (5) is optionally amplified by the modulation signal generator (13) and modulates the source signal (8) to generate a target modified modulated source signal (4).

The modulated source signal (10) as well as the target modified modulated source signal (4) is applied to the target by capacitive coupling and not by radiation or radiative coupling. The capacitive coupling is done between at least two conductive electrodes, i.e. at least one electrode and at least one counter-electrode, forcing RF-current between them. That means, the RF current runs between the at least two conductive electrodes. Thus, the device of the present invention uses conduction between the opposing electrode pair and does not use radiation between the electrodes forming the antenna.

The RF current running between the electrodes has the advantage that it finds the target area by itself and does not require any focusing. Furthermore the electric field generated between the conductive electrodes induces apoptosis and kills, for instance, cancer cells by apoptosis and not by necrosis like the radiative coupling does which also kills healthy cells and mostly kills healthy cells when the radiative treatment is not focused well.

It is very important to stress that in the radiation solution the selection of the treated area or the treated cells is global, i.e. all cells within a macroscopic area are killed by heating up said area, irrespective if the cells are cancerous or not. These common devices try to focus by phase modulation (phase array) the heat at the area where the solid tumor is so that preferably tumor cells are killed.

In contrast, in case of the device according to the present invention, the selection is made on the cellular level, it is automatic, due to using the cellular differences between healthy and tumorous or cancerous cells. This is why the metabolic rate differs between the healthy or normal cells and the tumorous or cancerous cells by their ionic environment and so by their impedance. Therefore it is also very important that due to this fact the device of the present invention is also useful to treat cancer metastates and not only solid tumors, since the state of the art devices need to focus their generated heat on a macroscopic or larger area and the inventive device can also kill singles cancer cells and cancer metastates due to a differentiation of the cells on a microscopic level.

Thus due to the use of an electric field (near field approximation) by the inventive RF hyperthermia device, where the electric field makes the effect at the cellular level (membrane distortion), the present device is superior to the common devices, which apply the radiative solution uses the Poynting vector (a vector product or magnetic and electric fields) which are only useful to generate only heating.

Moreover the present inventive device uses amplitude modulation and not phase as the common devices of the state of the art do.

The term "target" as used herein refers to the object (i.e. patient, human or animal) to be treated with hyperthermia or oncothermia.

The term "target area" refers to the body part of the target which is located between the electrodes and which comprises the malignant, diseases or painful area or tissue or cells.

The term "target tissue" refers to the malignant, diseases or painful tissue or cells.

Figure 14A:
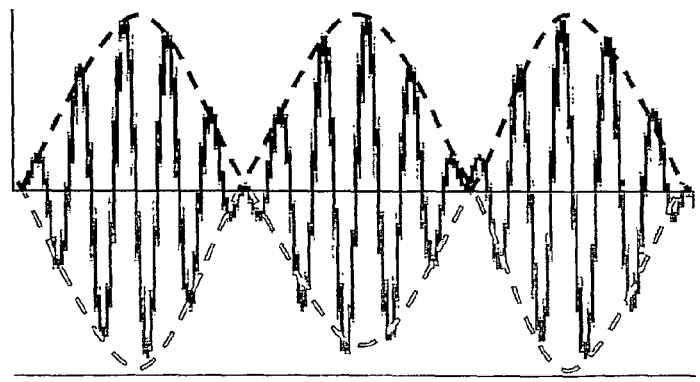
FIG. 14A shows an amplitude modulated signal and FIG. 14B shows the demodulated signal of FIG. 14A by cutting only the symmetric part of the modulated signal of FIG. 14A.
Figure 14B:
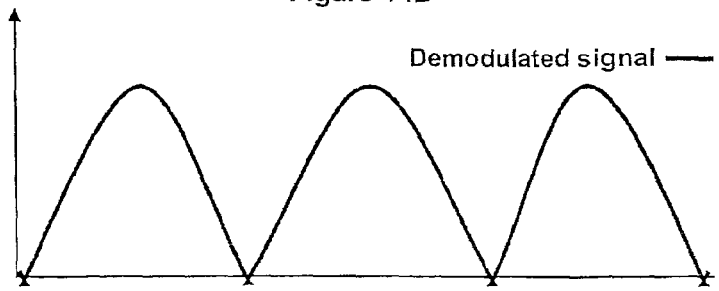

The modulation targets the adherent connections ("social signals") of a cell. Malignant cells act autonomous since their connections have been interrupted due to their time-fractal fluctuation. In contrast, healthy cells have such connections, they act collectively and are highly regulated in a time-fractal manner. The inventive signal modulation is very complex. After receiving the signal a demodulation (mining the info, detaching the carrier) is necessary. The easiest method consists in using an amplitude modulation-demodulation pair, as the modulation is only the change of the signal "strength" by the info to be carried and the demodulation is a simple rectification by cutting the symmetric signal (see FIG. 14).

Demodulation rectification needs asymmetry when a non-linear signal is received from the receiver. One solution approach for the demodulation problem consists in stochastic resonance. It is shown in this application that the amplitude-modulated signal can excite stochastic resonance.

In conclusion, each small amplitude modulation of the carrier frequencies (if the modulation is selected from the stochastic resonance frequency) could cause a defined resonant effect in every two-state Markovian situation (e.g. enzymatic processes, voltage-gated ionic channels, etc.). Due to the very high number of such possible reactions in a living organism, these microscopic effects lead to macroscopic results.

Figure 15:
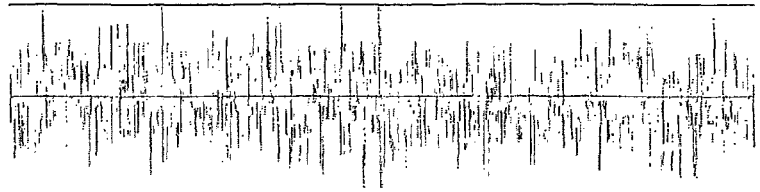
FIG. 15 shows the noisy environment (white noise)
Figure 16A:
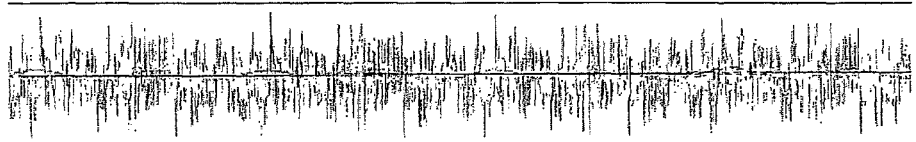
FIGS. 16 (A and B) show how a small deterministic signal is mixed (modulated or simply added) to the noise. Signal strength is much less than that of the noise. The difference between FIGS. 16A and 16B is that there are two deterministic signals (one high frequency and a low one) are added to the same white-nose spectra.
Figure 16B:
Figure 17A:
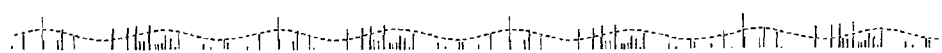
FIGS. 17A and 17B show that both of the two [low (17A) and high (17B) frequencies] deterministic signals could be "demodulated" by the way of stochastic resonance.
Figure 17B:

The sensitivity threshold application can serve as a simple explanation of a demodulation-like effect through stochastic processes. The white noise (uncorrelated, normal distribution around zero level) doesn't display any regular pattern (see FIG. 15). Adding (modulating) a deterministic signal with low or high frequency, but a low amplitude apparently does not change the character of the noise (see FIG. 16). However, if there is a sensitivity threshold cutting the amplitude mass of the wave and displaying only high suprathreshold amplitudes the amplitude modulation (or simple addition) becomes observable, and the deterministic signal could be reconstructed above threshold level (see FIG. 17). The threshold cut is not a real modulation, but it leads to the same effect. There is a minimum starting from which the suprathreshold signal becomes recognizable, and another level at which the threshold is so low that practically the complete noise can pass unfiltered, and a maximum in between these two levels.

The threshold with a fixed noise amplitude can be varied but in practice this threshold appears as being fixed in living objects. In this case the noise amplitude can be tuned up to reach the threshold on an appropriate level. Of course a mixture of deterministic waves also can be recognized on this way (see FIG. 17A and FIG. 17B).

It could be shown that there is an alternating field effect on enzyme activity and signal-transduction. In clinical trials it has been shown that an AC electric field can inhibit the metastatic spread of a solid lung tumor.

Direct application of low frequency current is also possible, without demanding any demodulation. The success of AC applications does not bias the modulation-demodulation approach because applying a carrier frequency serves to target a chosen structure (deep tissue, membrane effects, etc.). There are different views on modulation-demodulation.

The RF hyperthermia device of the present invention uses capacitive coupling, inductive coupling or radiative coupling and preferably capacitive coupling and alternating current (AC) and radio frequency (RF) waves.

In more detail the present invention is directed to a radiofrequency hyperthermia device which modulates the source radiofrequency (RF) signal (8) directed to a localised target area (17) and therefore increasing selectivity of the hyperthermia treatment of the localised target site. Preferably the RF signal (8) is a free industrial frequency like 13.56 MHz or the double or the triple of 13.56 MHz. The first modulation of the signal (8) is made by the modulator (9) which receives a modulation signal (12) from the modulation signal generator (13) and a source signal (8) from the signal generator (1) and converts these signals into a modulated signal (10) which is then amplified by the amplifier (2) and delivered as an amplified and modified signal to the targeted area (17). The modulation is preferably an amplitude modulation for inducing stochastic resonance demodulation, as outlined above. Modulation can also be achieved by impulses when the width and the time-sharing of the signal are modulated by the given noise (preferably "coloured" noise). The amplified and modulated signal, together with a reflected signal from the targeted area (17), are detected by a sensor (3) as the feedback from a first signal directed to the target area. This feedback signal (5) is directed to a feedback amplifier (6) if the feedback signal is not strong enough and required amplification. The amplified feedback signal (7) can then modify preferably through a further modulated signal (12) the source signal (8) emitted from the signal source (1) to produce a target modified signal (4). Also the amplified feedback signal (7) can provide feedback correction to the modulation signal provided by the modulation signal generator (13) at the multiplicator (11) to provide a further modulated signal (12) to the modulator (9) to produce a target modified signal (4).

The modulation signal source (13) is preferably a pink-noise (1/f noise) frequency generator. Pink noise has a fractal (time-domain) fluctuation, having long-range efficacy to act on the dynamical processes in a given target tissue/cell. It is preferably used for amplitude modulation.

The modulation signal (12) modulates the source signal (8) to create modulated signal (10) by amplitude modulation, frequency modulation or phase modulation. Preferably the signal is modulated by amplitude modulation, as outlined above.

In the inventive device of the present invention the sensor (3) is used to detect the feedback signal (5) from the target area (17) and this information is used to adjust the amplitude for an optimized modulation/demodulation process, the frequency spectrum (preferably pink noise) of the modulation signal (12) and modulate the carrier frequency (8) emitted by the signal source (1) via a feedback loop. The sensor (3) detects the standing wave ratio (SWR). This ratio measures the proper matching of the RF energy which is the ratio between the sum and the difference of the voltages of the transmitted and reflected signals.

$$\left(SWR = \frac{V_{forwarded} + V_{reflected}}{V_{forwarded} - V_{reflected}}\right).$$

The feedback sensor (3) can be placed before the target tissue (17), as shown in FIG. 6, or after the target tissue (17), as shown in FIG. 7. For example, as shown in FIG. 6 the sensor (3) is situated between the amplifier (2) and the target (17) or as shown in FIG. 7 the sensor (3) is situated between the target (17) and the feedback amplifier (6). However, the modulation of the signal must occur before the target tissue (17).

Signal checking unit (power/current sensor) (14), comparator to a reference signal ($P_a$(t)) (15) and reference signal ($P_a$(t)) (16) are optional additions to the inventive device which may serve for the fine-tuning of the feedback and the modulation.

Chelomey Pendulum Theory

The present invention uses the Chelomey pendulum theory for the modulation of the source signal (10). This theory can be described as follows:

The starting point is the non-linear differential equation $$L[x]=F(x,t)+f(x,t) \tag{1}$$

wherein L is a linear integro-differential operator.
The following restraints apply for functions F and f:
F changes slowly in time in relation to f,
F and f can be normalized, and the norm of f is small in relation to the norm of F,
f is a quasi-periodic function of t,
the mean value of f with respect to t equals to zero.
The mean value is generated by overline. So the solution of equation (1) in the $$x=X+\xi \tag{2}$$

form by satisfying the condition of $$\bar{x}=X \tag{3}$$

Then, supposing that the value of ξ is small (namely, the series expansion can be stopped at the second member), equation (1) can be set up in the form:

$$L[X] + L[\xi] = F(X, t) + \frac{dF}{dx}\bigg|_{x=X} \xi + f(X, t) + \frac{df}{dx}\bigg|_{x=X} \xi \tag{4}$$

By averaging the equation to the periodical time of the fast changing exciting member the average value is given by the solution of the equation $$L[X] = F(X, t) + \overline{\frac{df}{dx}\bigg|_{x=X} \xi} \quad (5)$$

Herein, it is applied that F changes slowly with time. Therefore, its average is equal to itself.

This equation can be solved if the $\xi(t)$ time function is known. As we supposed that $\overline{\xi}=0$, therefore, only the $F'(X,t)\xi+f(X,t)$ members of the equation can produce $-\xi$. Hereby, from (4) results the equation $$L[\xi] = \frac{dF}{dx}\bigg|_{x=X} \xi + f(X, t) \quad (6)$$

This is a linear differential equation on $\xi$. If it is supposed that X is a constant in this equation, as it changes slowly with time thus X will be the parameter of the solution. If f is sinusoidal it results $$f(X,t) = f_0(X) \sin \omega t \quad (7)$$

As the interest is in a steady solution the complex time functions in equation (6) are regarded.

$$L[\underline{\xi}] = \frac{dF}{dx}\bigg|_{x=X} \underline{\xi} + \underline{f}(X, t), \quad (8)$$
$$\underline{f}(X, t) = f_0(X) e^{j\omega t}$$

The solution of the equation is $$\underline{\xi} = \frac{\underline{f}(X, t)}{Z(\omega)} \quad (9)$$
$$= \frac{f_0(X) e^{j\omega t}}{Z(\omega)}$$
$$= Z(\omega) = \frac{L[e^{j\omega t}]}{e^{j\omega t}} - \frac{dF}{dx}\bigg|_{x=X}$$

By entering this into equation (5) the average solution is the differential equation $$L[X] = F(X, t) + \overline{\frac{df}{dx}\bigg|_{x=X} \xi} \quad (10)$$
$$= F(X, t) + \frac{1}{4|Z(\omega)|} \frac{df_0^2(X)}{dX} \cos\left(A \tan\left(\frac{\text{Im}Z(\omega)}{\text{Re}(Z(\omega))}\right)\right) =$$
$$= F(X, t) + \frac{1}{4|Z(\omega)|} \frac{df_0^2(X)}{dX} \frac{1}{\sqrt{1 + \left(\frac{\text{Im}Z(\omega)}{\text{Re}(Z(\omega))}\right)^2}}$$

from which can be concluded that a member changing rapidly with time might modify the solution of the equation. If this is not sinusoidal, but periodical then equation (8) has to be solved for each component. In this case (10) looks like this:

$$L[X] = F(X, t) + \overline{\frac{df}{dx}\bigg|_{x=X} \xi} \quad (11)$$
$$= F(X, t) +$$

-continued
$$\sum_i \frac{1}{4|Z(i\omega)|} \frac{df_{0i}^2(X)}{dX} \cos\left(A \tan\left(\frac{\text{Im}Z(i\omega)}{\text{Re}(Z(i\omega))}\right)\right)$$

The method can be similarly used for stochastical processes by applying a Fourier transformation. The above relationship can be rearranged into an equivalent form in order to generalize it for arbitrary signals.

$$L[X] = F(X, t) + \overline{\frac{df}{dx}\bigg|_{x=X} \xi} \quad (12)$$
$$= F(X, t) + \frac{1}{2} \text{Re}\left\{\sum_i \frac{1}{2} \frac{d\underline{f_{0i}}(X)\underline{f_{0i}^*}(X)}{dX} \left(\frac{1}{Z^*(i\omega)}\right)\right\}$$

From this, arbitrary signals result:

$$L[X] = F(X, t) + \overline{\frac{df}{dx}\bigg|_{x=X} \xi} \quad (13)$$
$$= F(X, t) +$$
$$\frac{1}{2} \text{Re}\left\{\frac{1}{2} \int_0^\infty \frac{d\underline{f_0}(X, \omega)\underline{f_0^*}(X, \omega)}{dX} \frac{1}{Z^*(\omega)} d\omega\right\}$$

Particularly, if the high-frequency excitation is pink noise, namely if $$\underline{f_0}(X, \omega)\underline{f_0^*}(X, \omega) = \frac{1}{\omega} f_{00}(X) f_{00}^*(X, \omega),$$

then results $$L[X] = F(X, t) + \overline{\frac{df}{dx}\bigg|_{x=X} \xi} \quad (14)$$
$$= F(X, t) +$$
$$\frac{1}{2} \text{Re}\left\{\frac{1}{2} \int_{\Omega^*}^\infty \frac{d\underline{f_{00}}(X)\underline{f_{00}^*}(X)}{dX} \frac{1}{\omega Z^*(\omega)} d\omega\right\}$$

wherein $\Omega^*$ is greater than the circular frequency of the other excitation member.

Application of this Method to Hyperthermia

In accordance with the conclusion outlined above the method can be applied if the rapidly changing excitation member depends on the solution of the equation. To apply this on hyperthermia the following items are needed: One first harmonic excitation which doesn't have to depend on the solution of the equation (hard source), and one or more upper harmonics. However, the superposition of the two sources has to be submitted to a capacity control, for example. Hereby, the applicability of Kapica's method is shown, f depends on the slowly changing solution of the equation. The following figure shows such a case, the amplitude modulation of the upper harmonic. Thus the rapidly changing excitation member depends on the solution.

Detailed Analysis of a Simple Case

The analyzed case can be applied to the displacement polarization. If the effect is of first-order, then $$f_0(X) \sin \omega t = f_{00} X \sin \omega t \quad (15)$$

and if a differential operator is chosen for the damped oscillation:

$$L[X] = \frac{d^2 X}{dt^2} + 2\beta\frac{dX}{dt} + \omega_0^2 X \quad (16)$$

The hard source shall not depend on X, so $$F(X,t) = F_0 \sin \Omega t \quad (17)$$

Then the equation looks like this:

$$Z(\omega) = \frac{L[e^{j\omega t}]}{e^{j\omega t}} = \omega_0^2 - \omega^2 + 2\beta j\omega \quad (18)$$

$$L[X] = \frac{d^2 X}{dt^2} + 2\beta\frac{dX}{dt} + \omega_0^2 X = \quad (19)$$
$$= F_0 \sin\Omega t + \frac{f_{00}^2 X}{4\sqrt{(\omega_0^2 - \omega^2)^2 + 4\beta^2\omega^2}} \cos\left[A r\tan\left(\frac{2\beta\omega}{\omega_0^2 - \omega^2}\right)\right]$$

The solution of the equation for a steady amplitude is:

$$A = \frac{F_0}{\sqrt{\left\{\left[\omega_0^2 - \frac{f_{00}^2}{4\sqrt{(\omega_0^2 - \omega^2)^2 + 4\beta^2\omega^2}}\cos\left[A r\tan\left(\frac{2\beta\omega}{\omega_0^2 - \omega^2}\right)\right]\right] - \Omega^2\right\}^2 + 4\beta^2\Omega^2}} \quad (20)$$

While for the phase shift:

$$\varphi = \quad (21)$$
$$A r\tan\left(\frac{2\beta\Omega}{\left[\omega_0^2 - \frac{f_{00}^2}{4\sqrt{(\omega_0^2 - \omega^2)^2 + 4\beta^2\omega^2}}\cos\left[A r\tan\left(\frac{2\beta\omega}{\omega_0^2 - \omega^2}\right)\right]\right] - \Omega^2}\right)$$

If X is the polarization and $F_0$ the electric field strength then the dielectric susceptibility equals to $$\varepsilon_0 \kappa = \frac{A}{F_0} = \quad (22)$$
$$= \frac{1}{\sqrt{\left\{\left[\omega_0^2 - \frac{f_{00}^2}{4\sqrt{(\omega_0^2 - \omega^2)^2 + 4\beta^2\omega^2}}\cos\left[A r\tan\left(\frac{2\beta\omega}{\omega_0^2 - \omega^2}\right)\right]\right] - \Omega^2\right\}^2 + 4\beta^2\Omega^2}}$$

As $\Omega$ is the circular frequency of the first harmonic excitation the focus is on $\omega$. Thus the susceptibility and the dielectric permittivity can be influenced since the second member of the denominator tunes the resonance frequency. The susceptibility can be significantly modified around the resonance of $\omega \approx \omega_0$, which is valid for its sign as well.

Additional Generalization

By the help of this the orientation polarization can be discussed. It is started from the non-linear, differential equation $$L[x] = G[F(x,t) + f(x,t)] \quad (23)$$

wherein L and G are linear integro-differential operators. The above described restrictions shall apply for the functions F and f. It is supposed that an inverse of the G operator exists and it is denoted by $G^{-1}$. Instead of (23) the following equation can be examined:

$$L^*[x] = G^{-1}L[x] = F(x,t) + f(x,t) \quad (24)$$

Then the solution will have the form $$x = X + \xi \quad (25)$$

thus satisfying the condition of $$\bar{x} = X \quad (26)$$

The equation $$L^*[\xi] = f(X,t) \quad (27)$$

stands for the rapidly changing part where it is supposed that $$\frac{dF}{dx} \approx 0.$$

On returning to original equation $$L[\xi] = G[f(X,t)] \quad (28)$$

the excitation $$f(X,t) = f_0(X)e^{j\omega t} \quad (29)$$

shall be harmonic. Therefore, it can be switched to the complex time functions $$L[\xi] = f_0(X)G[e^{j\omega t}] \quad (30)$$

wherein it has to be considered that X changes slowly with time in $f_0(X)$. The solution shall be found in the form $$\xi(X,t) = \xi_0(X)e^{j\omega t} \quad (31)$$

Then, the complex amplitude will be as follows:

$$\underline{\xi}_0(X) = f_0(X)\frac{G[j\omega]}{L[j\omega]} \quad (32)$$

Now the averaged time function results from the solution of the equation:

$$L^*[X] = F(X,t) + \overline{\frac{df}{dx}\bigg|_{x=X}\xi} \quad (33)$$
$$= F(X,t) + \frac{1}{4}\frac{df_0^2}{dX}\left|\frac{G(j\omega)}{L(j\omega)}\right|\cos A r\tan\left[\frac{\text{Im}\frac{G(j\omega)}{L(j\omega)}}{\text{Re}\frac{G(j\omega)}{L(j\omega)}}\right]$$

The results can be generalized to an arbitrary time function. First, the above relationship is rearranged to an equivalent form and generalized for the case of a line spectrum.

$$L[X] = F(X,t) + \overline{\frac{df}{dx}\bigg|_{x=X}\xi} \quad (34)$$
$$= F(X,t) + \frac{1}{2}\text{Re}\left\{\sum_i \frac{1}{2}\frac{d\underline{f_{0i}}(X)\underline{f_{0i}^*}(X)}{dX}\left(\frac{G(i\omega)}{Z(i\omega)}\right)^*\right\}$$

From this arbitrary signals result:

$$L[X] = F(X, t) + \overline{\frac{df}{dx}\Big|_{x=X}}\xi \qquad (34)$$
$$= F(X, t) + \frac{1}{2}\text{Re}\left\{\frac{1}{2}\int_0^\infty \frac{df_0(X, \omega)f_0^*(X, \omega)}{dX}\left(\frac{G(\omega)}{L(\omega)}\right)^* d\omega\right\}$$

Particularly, if high-frequency excitation is made by pink noise, namely, $$f_0(X, \omega)f_0^*(X, \omega) = \frac{1}{\omega}f_{00}(X)f_{00}^*(X, \omega) \text{ then} \qquad (36)$$

$$L[X] = F(X, t) + \overline{\frac{df}{dx}\Big|_{x=X}}\xi$$
$$= F(X, t) + \frac{1}{2}\text{Re}\left\{\frac{1}{2}\int_{\Omega^*}^\infty \frac{df_{00}(X)f_{00}^*(X)}{dX}\left(\frac{G(\omega)}{\omega L(\omega)}\right)^* d\omega\right\}$$

results wherein $\Omega^*$ is greater than the circular frequency of the other excitation member. If X is linear in $f_0(X)$ in equation (30) then the above equation takes up the form of $$L[X] + KG[X] = G[F(t)], \qquad (37)$$

$$K = -\frac{1}{2}\left(\frac{df_0}{dX}\right)^2\left|\frac{G(j\omega)}{L(j\omega)}\right|\cos A r\tan\left[\frac{\text{Im}\frac{G(j\omega)}{L(j\omega)}}{\text{Re}\frac{G(j\omega)}{L(j\omega)}}\right]$$

If the circular frequency $\omega$ is high then the high-frequency approximation can be used. If the excitation is harmonic with the complex time function $$\underline{F(t)} = F_0 e^{j\Omega t} \qquad (38)$$

then the complex amplitude will be as follows:

$$\underline{X}_0 = F_0 \frac{G[j\Omega]}{L[j\Omega] + KG[j\Omega]}, \qquad (39)$$

Figure 23:
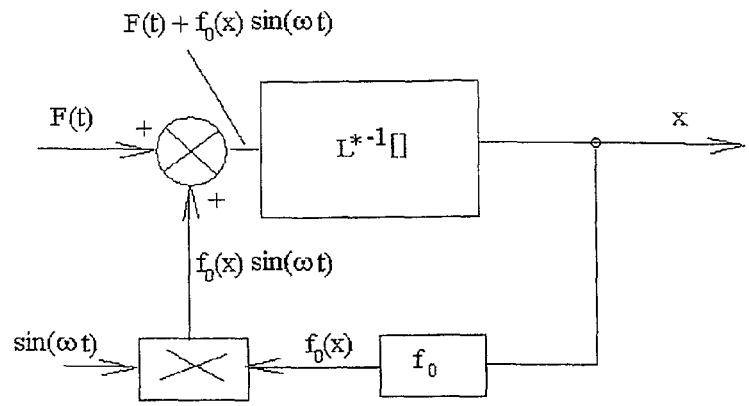
FIG. 23 shows the "Formation" of the Kapica equation.

It still remains open how the Kapica equation discussed above can be produced. A method for this is shown in the FIG. 23. As can be seen from FIG. 23 it can practically be spoken about a positive feedback where the feedback signal is submitted to a high-frequency full modulation.

Orientation Polarization of Debay

If effect is of first-order, namely $$f_0(X)\sin \omega t = f_{00} X \sin \omega t \qquad (40)$$

and if the differential operator of the damped oscillation is chosen as follows:

$$L[j\Omega] = j\Omega\tau + 1,$$

$$G[j\Omega] = j\Omega\varepsilon_\infty + \varepsilon_{r0} \qquad (41)$$

If there is no high-frequency excitation then $$X_0 = F_0 \frac{G(j\Omega)}{L(j\Omega)} = F_0 \frac{j\Omega\tau\varepsilon_\infty + \varepsilon_{r0}}{j\Omega\tau + 1} \qquad (42)$$

And the relative permittivity is $$\varepsilon = \frac{X_0}{F_0} = \frac{j\Omega\tau\varepsilon_\infty + \varepsilon_{r0}}{j\Omega\tau + 1} \qquad (43)$$

which corresponds to the Debay polarization. This can be seen in the case of low frequencies $$\varepsilon = \varepsilon_{r0} \qquad (44)$$

while for high frequencies $$\varepsilon = \varepsilon_\infty \qquad (45)$$

applies. In the case of Debay polarization the condition $$\varepsilon_\infty < \varepsilon_{r0} \qquad (46)$$

must be fulfilled. If there is a high-frequency excitation then the complex amplitude will be:

$$X_0 = F_0 \frac{G[j\Omega]}{L[j\Omega] + KG[j\Omega]} \qquad (47)$$
$$= F_0 \frac{j\Omega\tau\varepsilon_\infty + \varepsilon_{r0}}{j\Omega\tau(1 + K\varepsilon_\infty) + 1 + K\varepsilon_{r0}}$$

Then the permittivity is $$\varepsilon = \frac{j\Omega\tau\varepsilon_\infty + \varepsilon_{r0}}{j\Omega\tau(1 + K\varepsilon_\infty) + 1 + K\varepsilon_{r0}} \qquad (48)$$

In the case of low frequencies it can be seen that $$\varepsilon = \frac{\varepsilon_{r0}}{1 + K\varepsilon_{r0}} \qquad (49)$$

the case of high frequencies we get the permittivity $$\varepsilon = \frac{\varepsilon_\infty}{1 + K\varepsilon_\infty} \qquad (50)$$

In theory, it is possible that this high frequency permittivity is negative. The consequence would be a pushing out of force lines. This principle could be used for levitation. Namely by choosing the sign and magnitude of K the permittivity can be influenced. When the high frequency approximation is regarded it results that $$K = -\frac{1}{2}\left(\frac{df_0}{dX}\right)^2\left|\frac{G(j\omega)}{L(j\omega)}\right|\cos A r\tan\left[\frac{\text{Im}\frac{G(j\omega)}{L(j\omega)}}{\text{Re}\frac{G(j\omega)}{L(j\omega)}}\right] = \qquad (51)$$
$$= -\frac{1}{2}\left(\frac{df_0}{dX}\right)^2 \varepsilon_\infty$$

Herein, the sign does not depend on the sign of the derivative.

Rapidly Changing Excitation Depending on the Velocity

The non-linear differential equation $$L[x] = G\left[F(x,t) + f\left(\frac{dx}{dt}, t\right)\right] \quad (52)$$

shall be considered where L and G are linear integro-differential operators. The above-described restrictions shall remain valid for functions F and f. It is supposed that the inverse of the G operator exists and is denoted by $G^{-1}$. Instead of (23) the following equation can be examined:

$$L^*[x] = G^{-1}L[x] = F(x,t) + f\left(\frac{dx}{dt}, t\right) \quad (53)$$

A solution of the equation form $$x = X + \xi \quad (54)$$

shall be found wherein the condition of $$\bar{x} = X \quad (55)$$

shall be satisfied. For the rapidly changing part stands the equation $$L^*[\xi] = f\left(\frac{dX}{dt}, t\right) \quad (56)$$

where it is supposed that $$\frac{dF}{dx} \approx 0.$$

Now, when going back to the original equation $$L[\xi] = G\left[f\left(\frac{dX}{dt}, t\right)\right] \quad (57)$$

the excitation $$\underline{f}(X,t) = f_0(X)e^{j\omega t} \quad (58)$$

shall be harmonic. Therefore, it can be switched to the complex time functions $$L[\underline{\xi}] = f_0\left(\frac{dX}{dt}\right)G[e^{j\omega t}] \quad (59)$$

where it must be taken into consideration that $$\frac{dX}{dt}$$

changes slowly with time in $$f_0\left(\frac{dX}{dt}\right).$$

A solution shall be found for the form $$\underline{\xi}(X,t) = \underline{\xi}_0(X)e^{j\omega t} \quad (60)$$

Then the complex amplitude will be as follows:

$$\underline{\xi}_0(X) = f_0\left(\frac{dX}{dt}\right)\frac{G[j\omega]}{L[j\omega]} \quad (61)$$

The complex velocity amplitude is $$\frac{d\underline{\xi}_0(X)}{dt} = f_0\left(\frac{dX}{dt}\right)\frac{j\omega G[j\omega]}{L[j\omega]} \quad (62)$$

Now the averaged time function results from the solution of the equation $$L^*[X] = F(X,t) + \overline{\left.\frac{df}{d\frac{dx}{dt}}\right|_{\frac{dx}{dt}=\frac{dX}{dt}} \frac{d\xi}{dt}} \quad (63)$$

$$= F(X,t) + \frac{1}{4}\frac{df_0^2}{d\frac{dX}{dt}}\left|\frac{j\omega G(j\omega)}{L(j\omega)}\right|$$

$$\cos A r\tan\left[\frac{\mathrm{Im}\frac{j\omega G(j\omega)}{L(j\omega)}}{\mathrm{Re}\frac{j\omega G(j\omega)}{L(j\omega)}}\right]$$

If $$\frac{dX}{dt}$$

is linear in $$f_0\left(\frac{dX}{dt}\right)$$

then the above equation takes up the form of $$L[X] + KG\left[\frac{dX}{dt}\right] = G[F(t)], \quad (64)$$

$$K = -\frac{1}{2}\left(\frac{df_0}{d\frac{dX}{dt}}\right)^2\left|\frac{j\omega G(j\omega)}{j\omega L(j\omega)}\right|\cos A r\tan\left[\frac{\mathrm{Im}\frac{j\omega G(j\omega)}{L(j\omega)}}{\mathrm{Re}\frac{j\omega G(j\omega)}{L(j\omega)}}\right]$$

If the circular frequency $\omega$ is high then the high-frequency approximation might be used. If the excitation is harmonic with the complex time function $$\underline{F}(t) = F_0 e^{j\Omega t} \quad (65)$$

then the complex amplitude will be as follows:

$$X_0 = F_0 \frac{G[j\Omega]}{L[j\Omega] + Kj\Omega G[j\Omega]}, \tag{66}$$

The permittivity for the Debay case will be $$\varepsilon = \frac{j\Omega\tau\varepsilon_\infty + \varepsilon_{r0}}{j\Omega\tau(1 + K\varepsilon_{r0}) + 1 - K\Omega^2\tau\varepsilon_\infty} \tag{67}$$

In the case of low frequencies can be seen:

$$\in = \in_{r0} \tag{68}$$

In the case of high frequencies can be seen:

$$\in = 0 \tag{69}$$

Therefore, by applying such a control high-frequency capacitive shunting can be eliminated.

Rapidly Changing Excitation Depending on the Acceleration

This can happen, for example, if mass fluctuates at high-frequency. Classically, this method can be used if the fluctuating effect of vacuum shall be regarded. Starting point shall be the differential equation:

$$L[x] = G\left[F(x,t) + f\left(\frac{d^2x}{dt^2}, t\right)\right] \tag{70}$$

The above described restrictions shall remain valid for the functions F and f. It is supposed that the inverse of the G operator exists and is denoted by $G^{-1}$. Instead of (20) the following equation will be examined:

$$L^*[x] = G^{-1}L[x] = F(x,t) + f\left(\frac{d^2x}{dt^2}, t\right) \tag{71}$$

A solution of this equation shall be found in form (2) by specifying requirement (3). Then the solution will have the form $$x = X + \xi \tag{72}$$

thus satisfying the condition of $$\bar{x} = X \tag{73}$$

For the rapidly changing part the equation is $$L^*[\xi] = f\left(\frac{d^2X}{dt^2}, t\right) \tag{74}$$

where it is supposed that $$\frac{dF}{dx} \approx 0.$$

Now going back to the original equation $$L[\xi] = G\left[f\left(\frac{d^2X}{dt^2}, t\right)\right] \tag{75}$$

the excitation $$f(X,t) = f_0(X)e^{j\omega t} \tag{76}$$

shall be harmonic. Therefore, it can be switched to complex time functions as $$L[\underline{\xi}] = f_0\left(\frac{d^2X}{dt^2}\right)G[e^{j\omega t}] \tag{77}$$

where it is taken into consideration that $$\frac{d^2X}{dt^2}$$

changes slowly with time in $$f_0\left(\frac{d^2X}{dt^2}\right).$$

A solution shall be found for the form $$\underline{\xi}(X,t) = \underline{\xi}_0(X)e^{j\omega t} \tag{78}$$

Then the complex amplitude will be as follows:

$$\underline{\xi}_0(X) = f_0\left(\frac{d^2X}{dt^2}\right)\frac{G[j\omega]}{L[j\omega]} \tag{79}$$

The complex velocity amplitude is $$\frac{d\underline{\xi}_0(X)}{dt} = -f_0\left(\frac{d^2X}{dt^2}\right)\frac{\omega^2 G[j\omega]}{L[j\omega]} \tag{80}$$

Now the averaged time function results from the solution of the equation $$L^*[X] = F(X,t) + \frac{df}{d\frac{d^2x}{dt^2}}\bigg|_{\frac{d^2x}{dt^2} = \frac{d^2X}{dt^2}} \frac{d^2\xi}{dt^2} \tag{81}$$

$$= F(X,t) - \frac{1}{4}\frac{df_0^2}{d\frac{d^2X}{dt^2}}\left|\frac{\omega^2 G(j\omega)}{L(j\omega)}\right|\cos A\tan\left[\frac{\text{Im}\frac{-\omega^2 G(j\omega)}{L(j\omega)}}{\text{Re}\frac{j\omega G(j\omega)}{L(j\omega)}}\right]$$

If $$\frac{d^2X}{dt^2}$$

is linear in $$f_0\left(\frac{d^2X}{dt^2}\right)$$

then the above equation takes up the form $$L[X] + KG\left[\frac{d^2X}{dt^2}\right] = G[F(t)], \quad (82)$$

$$K = -\frac{1}{2}\left(\frac{df_0}{d\frac{d^2X}{dt^2}}\right)^2 \left|\frac{j\omega G(j\omega)}{j\omega L(j\omega)}\right| \cos A r \tan\left[\frac{\text{Im}\frac{j\omega G(j\omega)}{L(j\omega)}}{\text{Re}\frac{j\omega G(j\omega)}{L(j\omega)}}\right]$$

If the circular frequency ω is high then the high-frequency approximation might be used. If the excitation is harmonic with the complex time function $$\underline{F(t)} = F_0 e^{j\Omega t} \quad (83)$$

then the complex amplitude will be as follows:

$$\underline{X}_0 = F_0 \frac{G[j\Omega]}{L[j\Omega] - K\Omega^2 G[j\Omega]}, \quad (84)$$

Then the permittivity for the Debay case will be $$\varepsilon = \frac{j\Omega\tau\varepsilon_\infty + \varepsilon_{r0}}{j\Omega\tau(1 - K\Omega^2\varepsilon_\infty) + 1 - K\Omega^2\varepsilon_{r0}} \quad (85)$$

In the case of low frequencies it may be seen:

$$\in = \in_{r0} \quad (86)$$

and in the case of high frequencies:

$$\in = 0 \quad (87)$$

Consequently, by using this control capacitive shunting can be eliminated in the case of not too high frequencies as well. High-frequency control can also be combined. For example, the excitation might depend on displacement and velocity. In mechanics the same result is obtained by an accelerating coordinate system performing fast angular oscillations of low amplitude in which centrifugal and Coriolis force are applied.

Generalization of Kapica's Method for Vector Processes

At hyperthermia applications the person to be treated can be modelled by a layered dielectric material, wherein each layer is a parallel resistance-capacity coupling. Therefore, every layer is divariant. Consequently, it is important to generalize the theory to vector processes. The following equation shall be examined:

$$\underline{L}[\vec{X}] = \underline{G}[\vec{F}(t) + \vec{g}(\vec{X})f(t)] \quad (88)$$

If the matrix operator is invertible, then the above equation can be expressed in the form $$\underline{L}^*[\vec{X}] = \vec{F}(t) + \vec{g}(\vec{X})f(t),$$

$$\underline{L}^* = \underline{G}^{-1}\underline{L} \quad (89)$$

as well. If the solution function is factorised into an average (generated by the carrier-frequency signal) and a rapidly changing part (generated by the high-frequency signal):

$$\underline{L}^*[\vec{X} + \vec{x}] = \vec{F}(t) + \vec{g}(\vec{X} + \vec{x})f(t) = \quad (90)$$

$$= \vec{F}(t) + \vec{g}(\vec{X})f(t) + f(t)\vec{\nabla}\vec{g}\big|_{\vec{X}}\vec{x}$$

wherein accepted the Kapica's assumptions described earlier shall be assumed. The following two equations for the two parts of factorization result:

$$\underline{L}^*[\vec{X}] = \vec{F}(t) + \overline{f(t)\vec{\nabla}\vec{g}\big|_{\vec{X}}\vec{x}},$$

$$\underline{L}^*[\vec{x}] = \vec{g}(\vec{X})f(t) \quad (91)$$

If the high-frequency signal is sinusoidal:

$$\vec{g}(\vec{X})f(t) = \vec{g}(\vec{X})e^{j\omega t} \quad (92)$$

then the solution of the above equation is sinusoidal as well, and the complex amplitude can be calculated from the matrix equation $$\vec{\underline{x}}_0 = \underline{L}^*(j\omega)\vec{g}(\vec{X}) \quad (93)$$

By entering this into the first equation of (4) an average solution for the carrier-frequency results:

$$\underline{L}^*[\vec{X}] = \vec{F}(t) + \overline{f(t)\vec{\nabla}\vec{g}\big|_{\vec{X}} \text{Im}\left[\underline{L}^*(j\omega)\vec{g}(\vec{X})e^{j\omega t}\right]} = \quad (94)$$

$$= \vec{F}(t) + \frac{1}{2}\text{Re}\left[e^{j\omega t}\vec{\nabla}\vec{g}\big|_{\vec{X}}\left(\underline{L}^*(j\omega)\vec{g}(\vec{X})\right)^*\right]$$

If the second member of the right side of equation is a linear function of the average solution, namely $$\frac{1}{2}\text{Re}\left[e^{j\omega t}\vec{\nabla}\vec{g}\big|_{\vec{X}}\left(\underline{L}^*(j\omega)\vec{g}(\vec{X})\right)^*\right] = \underline{K}(j\omega)\vec{X} \quad (95)$$

then the previous equation will be linear:

$$\underline{L}^*[\vec{X}] = \vec{F}(t) + \underline{K}(j\omega)\vec{X} \quad (96)$$

If F is sinusoidal, that is $$\vec{\underline{F}}(t) = \vec{F}_0 e^{j\Omega t} \quad (97)$$

consequently the solution of (9) is $$\vec{\underline{X}}_0 = [\underline{L}^*(j\Omega) - \underline{K}(j\omega)]^{-1}\vec{F}_0 \quad (98)$$

If the dependence is not in accordance with (95) but depends on the velocity or acceleration then the solution will have the form $$\vec{\underline{X}}_0 = [\underline{L}^*(j\Omega) - \underline{j\Omega K}(j\omega)]^{-1}\vec{F}_0 \quad (99)$$

$$\vec{\underline{X}}_0 = [\underline{L}^*(j\Omega) + \Omega^2\underline{K}(j\omega)]^{-1}\vec{F}_0 \quad (100)$$

The equations can be generalized—as shown earlier—for several high-frequency excitation functions.

Detailed Analysis of Permittivity by Using Kapica's Method: Lossy Capacitor

If the field strength of capacitor is E then the current density $$j = \sigma E + \varepsilon\frac{\partial E}{\partial t} \quad (101)$$

will be generated. In the case of harmonic feeding the equation can be expressed as follows:

$$j = \sigma E + i\omega\varepsilon\varepsilon_0 E \qquad (102)$$

$$= i\omega\varepsilon_0\left(\varepsilon + \frac{\sigma}{i\omega\varepsilon_0}\right)E =$$

$$= i\omega\varepsilon_0\left(\varepsilon - i\frac{\sigma}{\omega\varepsilon_0}\right)E$$

$$= i\omega\varepsilon_0(\varepsilon' - i\varepsilon'')E$$

$$= i\omega\varepsilon_0\varepsilon E$$

The power dissipated in a unit volume equals to $$p = \frac{1}{2}\text{Re}(E^* \; j) = \frac{1}{2}\sigma|E|^2 = \frac{1}{2}\omega\varepsilon_0\varepsilon''|E|^2 \qquad (103)$$

where the asterisk denotes the conjugation.

Debay's Capacitor

Figure 24:
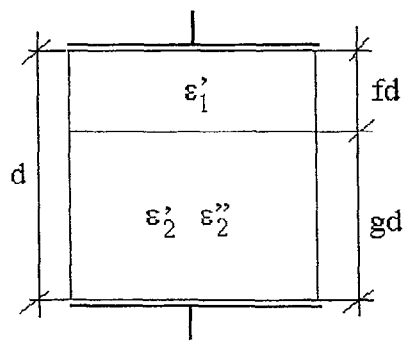
FIG. 24 shows the frequency dependence of the Debay's permittivity.

Let us take an ideal and lossy capacitor connected in series (see FIG. 24).

The resultant permittivity of the arrangement is $$\frac{1}{\varepsilon} = \frac{f}{\varepsilon_1'} + \frac{g}{\varepsilon_2} = \frac{f}{\varepsilon_1'} + \frac{g}{\varepsilon_2' - i\varepsilon_2''} \qquad (104)$$

This can be rearranged in the following way:

$$\varepsilon = \varepsilon' - i\varepsilon'' = \varepsilon_\infty + \frac{\varepsilon_s - \varepsilon_\infty}{1 + i\omega\tau}, \qquad (105)$$

$$\varepsilon_s = \frac{\varepsilon_1'}{f}, \; \varepsilon_\infty = \frac{\varepsilon_1'\varepsilon_2'}{f\varepsilon_1' + g\varepsilon_2'},$$

$$\tau = \frac{f\varepsilon_1' + g\varepsilon_2'}{\omega f \varepsilon_2''}$$

It is easy to show that the above form is identical with the form given before:

$$\varepsilon = \varepsilon' - i\varepsilon'' \qquad (106)$$

$$= \varepsilon_\infty + \frac{\varepsilon_s - \varepsilon_\infty}{1 + i\omega\tau} =$$

$$= \frac{\varepsilon_s + i\varepsilon_\infty \omega}{1 + i\omega\tau}$$

$$= \varepsilon_s \frac{1 + i\frac{\varepsilon_\infty}{\varepsilon_s}\omega\tau}{1 + i\omega\tau}$$

For specifying the loss by Debay's the complex permittivity has to be defined. From equation (105) results $$\varepsilon = \varepsilon' - i\varepsilon'' \qquad (107)$$

$$= \varepsilon_\infty + \frac{\varepsilon_s - \varepsilon_\infty}{1 + i\omega\tau}$$

$$= \frac{\varepsilon_s + i\varepsilon_\infty \omega^2\tau^2}{1 + \omega^2\tau^2} - i\frac{\omega\tau(\varepsilon_s - \varepsilon_\infty)}{1 + \omega^2\tau^2}$$

$$\varepsilon'' = \frac{\omega\tau(\varepsilon_s - \varepsilon_\infty)}{1 + \omega^2\tau^2}$$

Thus $$p = \frac{1}{2}\text{Re}(E^* \; j) \qquad (108)$$

$$= \frac{1}{2}\omega\varepsilon_0\varepsilon''|E|^2$$

$$= \frac{1}{2}\varepsilon_0\omega\frac{\omega\tau(\varepsilon_s - \varepsilon_\infty)}{1 + \omega^2\tau^2}|E|^2$$

High-Frequency Control of a Lossy Capacitor

Figure 25:
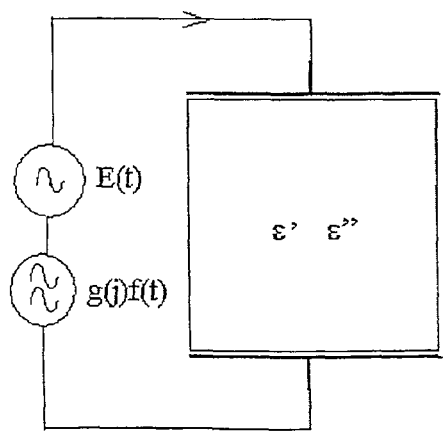
FIG. 25 shows the high-frequency control of lossy capacitor. E(t) refers to the carrier-frequency field strength and g(j)f(t) refers to the field strength depending on the high-frequency current density.

For the field strength of a capacitor a signal will be used which is proportional to the current density of the capacitor, but displaced in phase. The schematic diagram of this solution can be seen in FIG. 25.

In accordance with the preceeding for the arrangement of the figure the differential equation $$j = \sigma\left(1 + \tau\frac{d}{dt}\right)(E + g(j)f(t)), \qquad (109)$$

$$\tau = \frac{\varepsilon'}{\sigma}$$

results. From this—as described earlier—results $$G^{-1}[j] = E(t) + \frac{1}{2}\text{Re}\left[\frac{dg}{dj}g(j)G^*(i\omega)\right], \qquad (110)$$

$$G[] = \sigma\left(1 + \tau\frac{d}{dt}\right)$$

If the feeding is harmonic and if the second member is a homogeneous function of the current density the Kapica equation $$\underline{j} = E_0 G(i\Omega) + \underline{K}(\omega)G(i\Omega)\underline{j}, \qquad (111)$$

results the relative permittivity of which equals to $$\varepsilon(\Omega) = \frac{\underline{j}}{i\Omega\varepsilon_0 E_0} = \frac{1}{i\Omega\varepsilon_0}\frac{G(i\Omega)}{1 - \underline{K}(\omega)G(i\Omega)} \qquad (112)$$

Cases

1. Control proportional to the current density. In this case $K(\omega)$ is a real number smaller than one, so it results $$\varepsilon(\Omega) = \frac{\varepsilon' - i\frac{\sigma}{\varepsilon_0\Omega}(1 - K\sigma - K\sigma\tau^2\Omega^2)}{(1 - K\sigma)^2 + K^2\sigma^2\tau^2\Omega^2} \qquad (113)$$

$$= \frac{\varepsilon' - i\varepsilon''(1 - K\sigma - K\sigma\tau^2\Omega^2)}{(1 - K\sigma)^2 + K^2\sigma^2\tau^2\Omega^2}$$

1.a. If $\tau\Omega K\sigma \gg 1$, $K\sigma < 1$ then $$\varepsilon = \varepsilon' \frac{1}{K^2\sigma^2\tau^2\Omega^2} - i\varepsilon'' \frac{1}{K\sigma} \quad (114)$$

Consequently, the real part decreases while the imaginary part increases and changes its sign.

1.b. If $\tau\Omega K\sigma \ll 1$, $K\sigma \ll 1'$ then $$\varepsilon(\Omega) = \varepsilon' \frac{1}{(1-K\sigma)^2} + i\varepsilon'' \frac{1}{1-K\sigma} \quad (115)$$

Consequently, the real and the lossy part will increase.

2. Inversely phased control proportional to the current density. In this case $K(\omega)$ is a real number smaller than one. From equation (11) results $$\varepsilon(\Omega) = \frac{\varepsilon'(1-2K\sigma) - i\varepsilon''(1-K\sigma + K\sigma\tau^2\Omega^2)}{(1-K\sigma)^2 + K^2\sigma^2\tau^2\Omega^2} \quad (116)$$

2.a. If $\tau\Omega K\sigma \gg 1$, $K\sigma < 1$ then $$\varepsilon = \varepsilon' \frac{1-2K\sigma}{K^2\sigma^2\tau^2\Omega^2} - i\varepsilon'' \frac{1}{K\sigma} \quad (117)$$

Consequently, the real part decreases, while the imaginary part increases.

2.b. If $\tau\Omega K\sigma \ll 1$, $K\sigma < 1$ then $$\varepsilon(\Omega) = \varepsilon' \frac{1}{(1-K\sigma)^2} - i\varepsilon'' \frac{1}{1-K\sigma} \quad (118)$$

Consequently, the real (to a greater extent) and the lossy part will increase.

3. Control proportional to the current density with a phase-lead angle of 90°. In this case $\underline{K}(\omega)=iK$. The relative complex permittivity will be $$\varepsilon(\Omega) = \frac{\varepsilon' - i\frac{\sigma}{\varepsilon_0\Omega}}{1 + K\sigma\tau\Omega - iK\sigma} \quad (119)$$

3.a. If $K\sigma \ll 1$ then $$\varepsilon(\Omega) = \varepsilon' \frac{1}{1 + K\sigma\tau\Omega} - i\frac{\frac{\sigma}{\varepsilon_0\Omega}}{1 + K\sigma\tau\Omega} \quad (120)$$

In this case both permittivities decrease.

3.b. If $K\sigma\tau\Omega \gg 1$ then $$\varepsilon(\Omega) = \varepsilon' \frac{1}{K\sigma\tau\Omega} - i\varepsilon'' \frac{1}{K\sigma\tau\Omega} \quad (121)$$

Consequently, both permittivities decrease.

4. Control proportional to the current density with a phase-delay angle of 90°. In this case $\underline{K}(\omega)=-iK$.

$$\varepsilon(\Omega) = \frac{\varepsilon' - i\frac{\sigma}{\varepsilon_0\Omega}}{1 - K\sigma\tau\Omega + iK\sigma} \quad (122)$$

4.a. If $K\sigma \ll 1$ then $$\varepsilon(\Omega) = \frac{\varepsilon'}{1 - K\sigma\tau\Omega} - i\frac{\varepsilon''}{1 - K\sigma\tau\Omega} \quad (123)$$

Therefore, both permittivities increase.

4.b. If $K\sigma\tau\Omega \gg 1$ then $$\varepsilon(\Omega) = -\varepsilon' \frac{1}{K\sigma\tau\Omega} + i\varepsilon'' \frac{1}{K\sigma\tau\Omega} \quad (124)$$

Consequently, both permittivities will change the sign and decrease.

High-Frequency Control of the Debay's Capacitor

The control is made according to the figure above, the only difference is the use of a Debay's capacitor. The relationship between the current density and field strength of the capacitor is as follows:

$$j = i\omega\varepsilon\varepsilon_0 E = \quad (125)$$
$$= i\omega\varepsilon_0 \frac{\varepsilon_s + i\varepsilon_\infty\omega}{1 + i\omega\tau} E$$
$$= i\omega\varepsilon_s \frac{1 + i\frac{\varepsilon_\infty}{\varepsilon_s}\omega\tau}{1 + i\omega\tau} E$$

If the $$\frac{d}{dt}$$

differential operator is entered instead of $i\omega$ the motion equation $$\left(1 + \tau\frac{d}{dt}\right)j = \varepsilon_s\varepsilon_0 \frac{d}{dt}\left(1 + \tau_1\frac{d}{dt}\right)(E + g(j)f(t)), \quad (126)$$
$$\tau_1 = \frac{\varepsilon_\infty}{\varepsilon_s}\tau$$

results wherein the presence of high-frequency excitation was taken into account. For the sake of simplicity the following operators will be introduced:

$$L[j] = G[E + g(j)f(t)], \quad (127)$$
$$L[] := \left(1 + \tau\frac{d}{dt}\right), G[] := \varepsilon_s\varepsilon_0 \frac{d}{dt}\left(1 + \tau_1\frac{d}{dt}\right)$$

From this it results for the rapidly changing part in the case of harmonic excitation that the complex amplitude of current density is $$\underline{j}_{gy} = g(j)\frac{G(i\omega)}{L(i\omega)} \tag{128}$$

For the carrier-frequency part:

$$L[j] = G\left[E(t) = \frac{1}{2}\text{Re}\left[\frac{dg}{dj}g(j)\left(\frac{G(i\omega)}{L(i\omega)}\right)^*\right]\right], \tag{129}$$

If the field density is harmonic and the second member on the right side of the equation is a homogeneous linear function of the current density then the algebraic equation $$L(i\Omega)\underline{j} = E_0 G(i\Omega) + \underline{K}(\omega)G(i\Omega)\underline{j} \tag{130}$$

from which the complex relative permittivity is:

$$\underline{\varepsilon} = \frac{\underline{j}}{i\Omega\varepsilon_0 E_0} = \frac{1}{i\Omega\varepsilon_0}\frac{G(i\Omega)}{L(i\Omega) - \underline{K}(\omega)G(i\Omega)} \tag{131}$$

After performing the conversions results $$\underline{\varepsilon} = \frac{\varepsilon_s(1 + i\Omega\tau_1)}{(1 + i\Omega\tau) - \underline{K}(\omega)\varepsilon_0\varepsilon_s i\Omega(1 + i\Omega\tau_1)} = \\ = \varepsilon_e \frac{1}{1 - i\Omega\varepsilon_0\varepsilon_e \underline{K}(\omega)} \tag{132}$$

wherein $\varepsilon_e$ is the original relative permittivity.

Cases

1. Control proportional to the current density. In this case $K(\omega)$ is a real number smaller than one. Thus $$\underline{\varepsilon} = \varepsilon_e \frac{1}{1 - i\Omega\varepsilon_0\varepsilon_e K} \\ = \varepsilon_e \frac{1}{1 - i\Omega\tau_v} \\ = \varepsilon_e \frac{1 + i\Omega\tau_v}{1 + \Omega^2\tau^2 v} \tag{133}$$

wherein $\tau_v = \varepsilon_0 \varepsilon_e K$. If $\tau_v = \tau$ then $$\underline{\varepsilon} = \varepsilon_e \frac{1}{1 - i\Omega\varepsilon_0\varepsilon_e K} \\ = \varepsilon_e \frac{1}{1 - i\Omega\tau_v} \\ = \varepsilon_e \frac{\varepsilon_s}{1 + \Omega^2\tau^2}(1 + i\Omega\tau_1) \tag{134}$$

From this it can be observed that the low-frequency permittivity remains unchanged, the high-frequency permittivity converges to zero, the imaginary part is negative and $$\varepsilon'' = -\frac{\varepsilon_s}{\Omega}\frac{\tau_1}{\tau} \tag{135}$$

2. Inversely phased control proportional to the current density. In this case $K(\omega)$ is a negative real number smaller than one. Thus $$\underline{\varepsilon} = \varepsilon_e \frac{1}{1 + i\Omega\varepsilon_0\varepsilon_e K} = \varepsilon_e \frac{1}{1 + i\Omega\tau_v} \tag{136}$$

wherein $\tau_v = \varepsilon_0 \varepsilon_e K$. If $\tau_v = \tau_1$ then $$\underline{\varepsilon} = \frac{\varepsilon_s}{1 + i\Omega\tau} = \frac{\varepsilon_s}{1 + \Omega^2\tau^2}(1 - i\Omega\tau) \tag{137}$$

From this it can be observed that the low-frequency permittivity remains unchanged, the high-frequency permittivity converges to zero, and the imaginary part is $$\varepsilon'' = \frac{\varepsilon_s}{\Omega} \tag{138}$$

3. Control proportional to the current density with a phase-lead angle of 90°. Then $\underline{K}(\omega) = iK$, and therefore $$\underline{\varepsilon} = \varepsilon_e \frac{1}{1 + \Omega\varepsilon_0\varepsilon_e K} = \varepsilon_e \frac{1}{1 + \Omega\tau_v} \tag{139}$$

It follows from this that the Debay's capacitor does not change at low-frequency but at high-frequency:

$$\varepsilon = \frac{\varepsilon_e}{\Omega\tau_v} \tag{140}$$

Consequently, the permittivity of the real and imaginary part decreases.

4. Control proportional to the current density with a phase-delay angle of 90°. In this case $\underline{K}(\omega) = -iK$, thus $$\underline{\varepsilon} = \varepsilon_e \frac{1}{1 - \Omega\varepsilon_0\varepsilon_e K} = \varepsilon_e \frac{1}{1 - \Omega\tau_v} \tag{141}$$

It follows from this that the Debay's capacitor does not change at low-frequency but at high-frequency:

$$\varepsilon = -\frac{\varepsilon_e}{\Omega\tau_v} \tag{142}$$

Consequently, the permittivity of the real and imaginary part decreases and changes its sign. The technical feasibility of the examined control cases hasn't been described yet. In principle, the implementation is simple. The slowly changing current of the capacitor shall be detected. The current shall be displaced in phase by a phase-shifter. The signal generated in this way shall be transformed into potential by a volt-ampere converter, and has to be multiplied by a rapidly changing sinusoidal signal. This signal shall be added to the low-frequency signal.

The modulated signal improves the treatment as fractal physiology creates special noise characteristics as a "social signal" in biological objects. Malignant cells have autonomy (named renegades by Weinberg) and are in permanent competition with others for nutrition and life-conditions. Healthy cells are generally collective, their control is made by "social signals", no real competition is introduced, only a labor division is active. This means that the active ionic exchange near the malignant cells (in most of the cases) is more intensive than in their healthy counterpart. These signals are different in the cancerous and healthy tissues. The signal absorption and signal feedback depends on the tissue properties optimizing the selective absorption. The most important parameter for effective target tissue treatment is the SWR measurement which exactly measures to which degree the target absorbs the actual frequency.

The pink noise generator modulation adds to the effect of the modulated signal on the target tissue as most of the healthy physiological effects have pink-noise signal exchange, while the malignant tissue does not, thus the pink noise modulation is selectively damaging to malignant tissue. Living systems are open dynamical structures, performing random stationary stochastic self-organizing processes. The self-organizing procedure is defined by the spatial-temporal-fractal structure, which is self-similar both in space and time. A special noise (called pink-noise, temporal fractal noise)—as a fingerprint of the self-organizination—is a typical and general behavior of living biomaterial, except randomly organized tumor cells. The bio-system is based on cyclic symmetry and has infinite degrees of freedom arranged by self-organizing principles. On this basis a new approach of the living state has been developed: The fractal physiology. In the living systems stochastic processes exist instead of deterministic actions, so predictions always have random, unpredictable elements.

This power spectrum characterizes the so-called pink-(1/f-, or flicker-) noise. In general, a stationary self-similar stochastic process follows the pink-noise if its power spectral density function is proportional to 1/f. Due to the self-similarity and to the stationary stochastic processes of biosystems, all of them are a priori pink-noise generators. However, a randomly structured tumor has no such property. The white noise-excited linear system with infinite degrees of freedom and cyclic symmetry emits pink noise. It works like a special filter creating 1/f noise from the non-correlated white noise spectrum measured before. The tumorous system has no such filtering. Therefore the pink noise generator modulation is essential for cancer treatment however for other diseases (e.g. when cell organization is not random) another spectrum could be useful.

Figure 3:
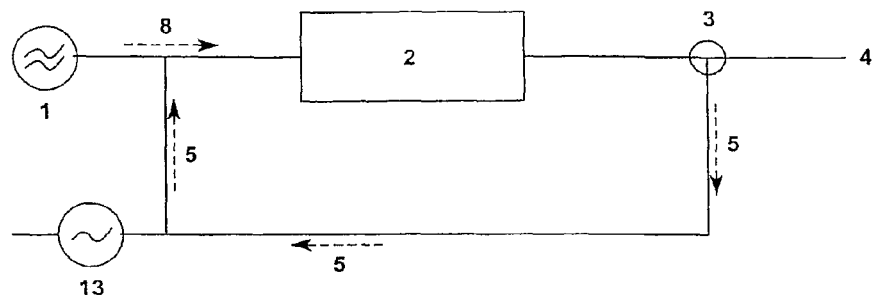
FIG. 3 shows an embodiment of the present invention with a modulation signal generator (13) and without a feedback amplifier (6)
Figure 4:
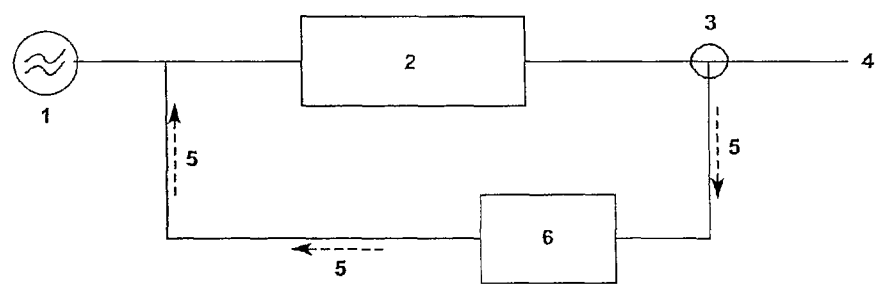
FIG. 4 shows an embodiment of the present invention without a modulation signal generator (13) and with feedback amplifier (6)

Thus it is also possible for the inventive device to be operated without a feedback amplifier (6) or without a modulation signal generator (13) such as a pink noise generator as shown in FIGS. 3 and 4. This would result in a mixed spectrum modulation which could be used and is used for applications other than tumour treatment, such as for pain management, disorders of the central nervous system and other disorders where the exchange of biological information between the cells and parts of the body is faulty. Pain killing by heat has been already observed by ancient doctors and can also be achieved by hyperthermia applications) and by an electric field (TENS effect). All the patients with tumor had experienced the pain killing of the oncothermia treatment using the inventive device, and they report relaxed, convenient treatment time, in most of the cases they fall asleep during the one-hour treatment process.)

In contrast no modulation is introduced in conventional devices. The aim in conventional hyperthermia is to reach the highest possible temperature and for that the source carrier frequency is enough.

The modulation of the source signal frequency (8) by the feedback signal (5) has the advantages of:

The additional information gained from the feedback provides an information boost in comparison to the simple unselective power treatment. This information makes it possible to select and optimize the actual energy distribution and to render the actual energy delivered to the target tissue more effective. Consequently, the inventive hyperthermia device is able to selectively heat target tissue which might be tumorous, cancerous, malignant, inflamed or otherwise from normal or healthy tissue distinguishable tissue. The inventive device does not unselectively heat a body area comprising target tissue but also normal or healthy tissue without differentiation. Consequently the modulation used within the present invention increases the target tissue specificity and consequently the selective generation of heat within the target tissue while heating or unnecessary heating of the surrounding normal or healthy tissue can be avoided or vehemently reduced.

In the case of hyperthermia treatment of tumour tissue using conventional devices the power alone heats both healthy tissue and tumour tissue unselectively and heats all tissues according to the law of the absorption of electromagnetic waves of a given frequency, power and of course the target material. Thus in classical hyperthermia the complete tissue is heated and success depends on the differing sensitivities of healthy tissue and tumour tissue to heat while heating the healthy tissue around the tumour tissue supports tumour growth and proliferation of cancer cells due to the increased delivery of nutrients to the diseased tissue due to increased blood flow. Consequently it is not desired to heat the healthy tissue in vicinity to the diseased and especially tumorous or cancerous tissue.

The temperature is an intensive equilibrium parameter. The physiology, mainly the blood flow and lymph flow, quickly makes it homeostatic (stationary equilibrium), irrespective of its effect on healthy and cancerous cells. This means, the effect of hyperthermia achieved with common hyperthermia devices is selective only due to the self-selection of the cells: The collective healthy cells tolerate more stress than the individual cancerous cells due to their collective interactive and stress-relaxing facilities. In chemo-thermo-therapies the role of chaperone proteins is important. Chaperones (stress- or heat-shock-proteins (HSP)) are highly conserved proteins, which are vital in almost every living cells and are located on their surfaces during their whole lifetime, regardless the evolutionary stage. With any kind of change (environmental stresses, various pathogen processes, diseases, etc.) the dynamic equilibrium of the cell activates their synthesis. Excretion of chaperones is a 'stress-answer' of cells to accommodate themselves to new challenges. As a consequence of the stress malignant cells undergo chaperones are present in all cancerous cells for adapting to the current stress, thus helping tumor-cells to survive. Moreover, heat shock-proteins are induced by all oncologic treatment methods aiming at eliminating the malignancy, such as conventional hyperthermia, chemotherapy and radiotherapy. Even phototherapy was shown to induce HSP synthesis. When adapting to the stress the induction or over-expression of HSP in general provides effective protection for the cell against apoptosis, but when located on the extracellular side of the cell membrane they have an opposite effect: They represent a signal to the immune system that there is a defect in the respective cell. Furthermore, induction of various HSPs (HSP27, HSP70, HSP90) was observed in numerous metastases and the HSP90 homologue GRP94 may act as a mediator of metastasis generation. HSPs in general diminish the effect of hyperthermia therapy by increasing tumor cell survival. A strong induction may generate a kind of thermotolerance of the tumor, and in parallel a drug- and radio-tolerance. Heat treatment can also lead to multi-drug resistance.

Less stress-tolerance of tumor tissue is the selective idea of most of the conventional systemic administered chemotherapies. The selection is not inherent to the chemistry of the drug, but instead relies mainly on the chemistry of healthy cells and the cellular structure of cancerous tissue.

Thus the present invention displays an important difference: The input energy carries information and is selective at least in synergy with the selective factors of the targeted cellular structures. Therefore when using the inventive device focusing the energy onto a target tissue is not as important as it is in classical hyperthermia, because the inventive device provides for self-selection, i.e. a form of autofocusing.

Consequently the present invention is also directed to a modulation feedback circuit comprising a feedback amplifier (6) for amplifying the feedback signal (5), preferably but optionally a multiplicator (11) to provide a further modulated signal (12) to the modulator (9), a sensor (3) for detecting the reflected or the transmitted signal from the target area (17), a modulation signal generator (13) which is preferably a pink noise generator for modulating or further modulating the feedback signal (5) and a modulator (9) for receiving a modulation signal (12) from the modulation signal generator (13). The modulation signal (12) is generated by the modulation signal generator (13) from the feedback signal (5) by modulating the feedback signal (5).

In this regard, the present invention also relates to the use of a modulation feedback circuit comprising a feedback amplifier (6) for amplifying the feedback signal (5), a sensor (3) for detecting the reflected or the transmitted signal from the target (17), a modulation signal generator (13) for modulating or further modulating the feedback signal (5) and for generating a modulation signal (12) for the manufacture of the radiofrequency hyperthermia device according to any one of claims 1-8 useful for the prophylaxis, treatment and after-treatment of tumours, cancer, metastases, carcinomas, pain, migraine and diseases of the central nervous system. The modulation feedback circuit may further comprise a modulator (9) for receiving the modulation signal (12) from the modulation signal generator (13).

Again, if the feedback signal (5) is strong and does not require amplification the feedback amplifier (6) is not mandatory and consequently, the present invention relates to the use of a modulation feedback circuit comprising a sensor (3) for detecting the reflected or the transmitted signal from the target (17), a modulation signal generator (13) for modulating or further modulating the feedback signal (5) and for generating a modulation signal (12) for the manufacture of the radiofrequency hyperthermia device according to any one of claims 1-8 useful for the prophylaxis, treatment and after-treatment of tumours, cancer, metastases, carcinomas, pain, migraine and diseases of the central nervous system. The modulation feedback circuit may further comprise a modulator (9) for receiving the modulation signal (12) from the modulation signal generator (13).

This modulation feedback circuit is used for the manufacture of the inventive RF hyperthermia device useful for the treatment and after-treatment of tumors, cancer pain, migraine and diseases of the central nervous system as well as for the prophylaxis of pain, migraine, cancer formation, tumor formation and the development of diseases of the central nervous system.

Moreover, the present invention relates to a RF hyperthermia device comprising a modulation signal generator (13) which is preferably a pink noise generator for modulating the signal (4) which is applied to the target area (17), wherein the signal (4) is modulated in a way that the selectivity for the target tissue is increased so that selectively the target tissue and not the surrounding healthy tissue is warmed-up or heated to up to 42° C. preferably 45° C.

Thus the present invention relates also to the use of a modulation signal generator (13) for the manufacture of a RF hyperthermia device for the treatment and after-treatment of tumors, cancer pain and diseases of the central nervous system.

Furthermore the present invention relates to a method for treating diseased tissue, especially tumorous, cancerous, malignant, inflamed or otherwise from normal or healthy tissue distinguishable tissue, by applying a modulated signal (4) to the diseased tissue wherein the modulated signal (4) is able to selectively warm-up or heat the diseased tissue while the surrounding healthy tissue is not directly warmed-up or heated by the applied RF waves.

The modulation of the source signal frequency (8) by the modulation signal generator (13) has the advantages of:

1. Healthy information exchange functions according the well known fact from fractal physiology of the dynamics of healthy biological processes that the long-term entropy fluctuation is equal in all areas. The energy uptake in non-pink noise areas will be higher than in pink noise areas. The social signal connection on the other hand will be well supported in the pink areas. Thus heating occurs selectively in non-pink noise areas only.

Figure 28:
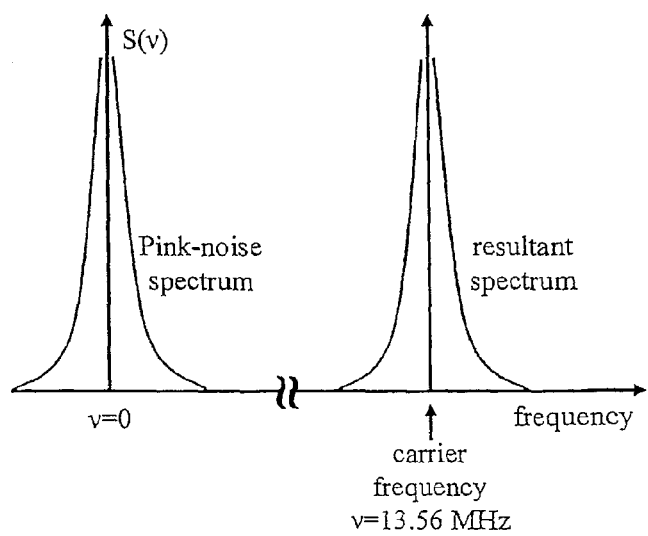
FIG. 28 Shows the modulation which makes a frequency distribution around the carrier frequency (13.56 MHz), which increases the amplitude (electric field) in the area.

2. The modulation increases the electric field gradient in the extracellular liquid, which aligns large protein molecules. The modulation makes a frequency distribution around the carrier frequency (13.56 MHz, see FIG. 28), which increases the amplitude (electric field) in the area. This order makes the social signal available (apoptosis induction) and "glues" the dividing cells into a fixed position (metastasis block).

Figure 18:
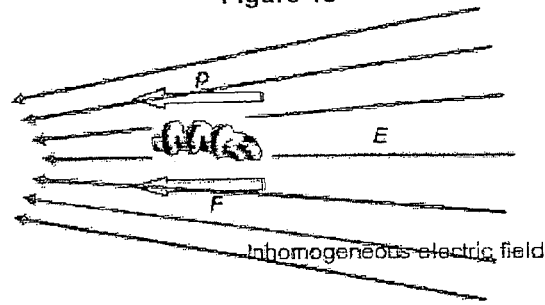
FIG. 18 shows the electric field E) which generates a dielectrophoretic cataphoretic force (F) on a biomolecule such as E-cadherin having a dipole moment p.
Figure 19:
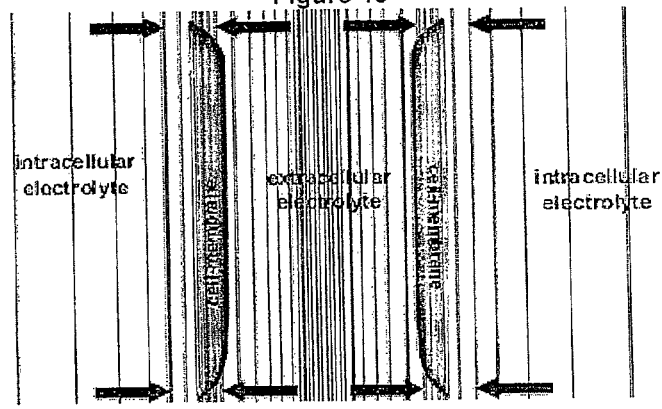
FIG. 19 shows that due to the electric field E), the dielectrophoretic cataphoretic force (F) and due to the dipole moment p of the molecule, perpendicular to the cell-membrane an inhomogeneous force-field is developed.

As described before, the electric current density is concentrated in the extracellular electrolyte, as well as due to the beta-dispersion the specific absorption rate (SAR) is high in the membrane. Perpendicular to the cell-membrane an inhomogeneous force-field is developed, (see FIG. 19.). This field E) generates a dielectrophoretic cataphoretic force (F) according to Formula (A) (see FIG. 18.) the molecules having a dipole moment p:

$$\underline{F} = (\underline{p} \cdot grad)\underline{E}$$  Formula (A)

Figure 20:
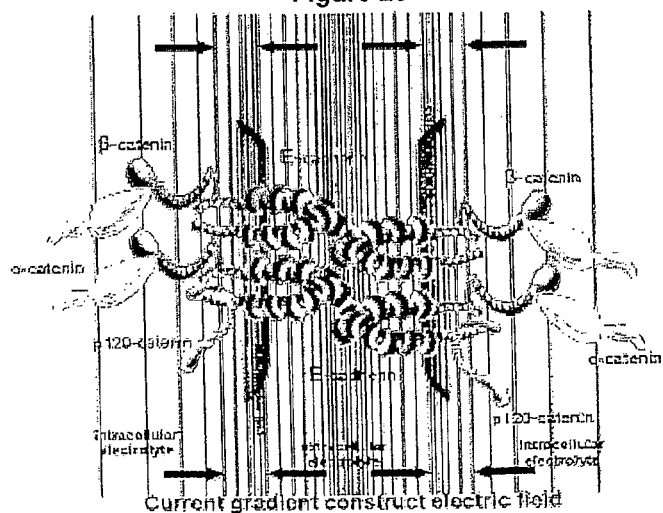
FIG. 20 shows that the cataphoretic forces allow the E-cadherin dimers on the membrane surface to bind to each other, thus connecting the dimers with each other.

The cataphoretic forces (well-oriented domains, dimers) of such large molecules like E-cadherin on the membrane surface allow them to bond again (see FIG. 20.), thus connecting the dimers with each other. The gradient inside the cell leads to an orientation of the beta-catenins and other anchor proteins (e.g. p120 catenin) to connect with the actin or filament network of the cell.

Figure 21:
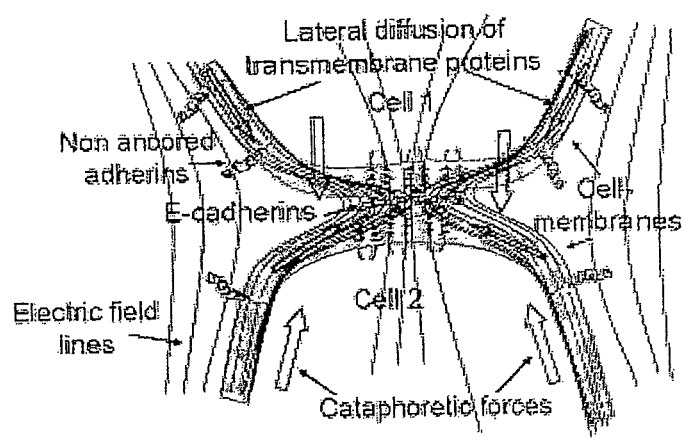
FIG. 21 shows that the electric field E) creates attraction forces between adjacent membranes of two cells.

The electric field causes three effects (see FIG. 21.):
1) Promoting the bond of non-connected adherins (decreasing the dissociation reaction constant $k_D$),
2) Increasing the activation energy (barrier $E_0$) and decreasing the dissociation reaction constant $k_D$),
3) Creating attraction forces between nearby membranes (decreasing the force f of a single bond).

Figure 22:
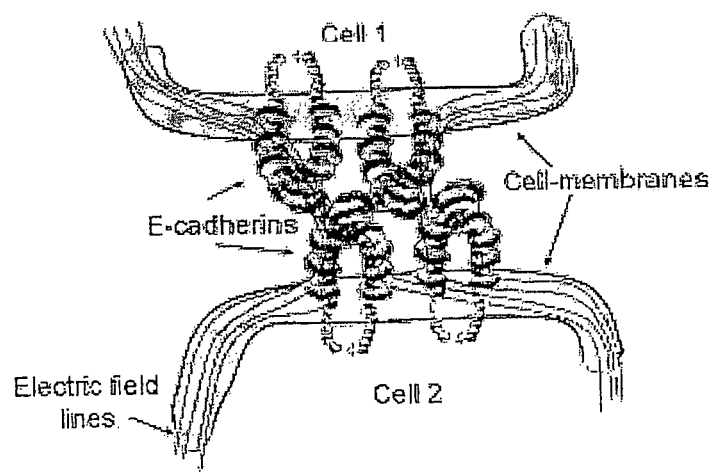
FIG. 22 shows that at the established connections the field-lines are conducted by the cadherins which have an extremely high relative permittivity which creates "hot-spots" on the membrane and promotes membrane damage.

At established connections the field-lines are conducted by the cadherins which have an extremely high relative permittivity (sometimes few thousand) (see FIG. 22.). This creates again "hot-spots" on the membrane and promotes membrane damage.

The effect of promoting adherent connections is directly opposed to the dissociation forced by the increasing temperature. Thus there is a clear difference of oncothermia from classical heat therapies.

Concerning the modulation, the modulation could act effectively on pain receptors, thus helping to suppress cancer-pain (a typical TENS (transcutan electric nerve stimulation) effect).

Pink noise modulation is preferable, but the pink noise spectrum is not necessary in all cases.

The combination of modulation of the source signal frequency (8) by the feedback signal (5) and modulation of the source signal frequency (8) by the modulation signal generator (13) provides the advantages of:

1. The feedback signal enables an application of the modulation as strongly or weakly as necessary, thereby personalising the energy delivered to the target tissue in real time. Patients and tumors are individual and have their own special impedance. The electric circuit from which the patient is a part (the patient is the condenser with the fitted electrodes) is optimized in every single case for the actual impedance and corrected also by its changes during treatment.

2. The feedback signal allows for the use of the Chelomey (Kapica) effect to stabilize the distortion mechanisms and optimize the killing of malignant cells.

Thus the present invention is directed to a radiofrequency hyperthermia device comprising a radiofrequency source (1), an amplifier (2), a sensor (3), a feedback amplifier (6) and a modulation signal generator (13) wherein the radiofrequency source produces a source signal (8) which is modulated by the modulation signal generator (13) to generate a modulated source signal (10), the modulated source signal (10) is amplified by the amplifier and directed to a target (17), and the sensor receives a feed back signal (5) from the target that is directed to the feed back amplifier, wherein the feedback signal is amplified by the feedback amplifier and modulates the source signal to generate a target modified modulated signal (4).

Preferably the feedback signal (5) modulates the modulation signal from the modulation signal generator (13). Further preferably the source signal (8) is modulated by the modulation signal from the modulation signal generator (13) that has been modulated by the feedback signal (5). Preferably the modulation signal generator (13) is a pink noise generator. Preferably sensor (3) is situated between the amplifier (2) and the target (17) or alternatively sensor (3) is situated between the target (17) and the feedback amplifier (6). Preferably the amplitude and frequency spectrum of the source signal is modulated.

The preferred frequency for use in the present invention is in the range of all the frequencies which are able to modulate the carrier frequency, usually up to a tenth of the carrier frequency. Most preferred is the audio range of 5-20,000 Hz because the resonance effects of biosystems lie in the audio range.

The preferred power for use in the present invention is in the range of 30 to 1500 W. Most preferred is the range of 60-250 W. This range is particularly safe and provides enough power for heating up the lesion. Tumor size (in the case of large tumors) does not exceed 1 liter in volume. For heating it up from body temperature to 40-45° C. (with a gradient of less than 10° C. per hour) even 250 W would be too much. This is only a provision for the case of high vascularisation in the tumor which may lead to a significant blood-cooling effect.

The hyperthermia device of the present invention can be an electric field coupled energy transfer device (capacitive coupling device), a magnetic field coupled energy transfer device (inductive coupling device), or a radiative energy transfer device (radiative coupling or antenna array device). Preferably the radiofrequency hyperthermia device of the present invention is an electric field coupled energy transfer hyperthermia device (capacitive coupling device).

The preferable device also has an applicator electrode. The applicator electrode can be a conventional bolus electrode where an active electrode is partnered with a counter electrode and the target tissue is placed between the active electrode and the counter electrode. Alternatively, the applicator electrode can be an electrode arrangement which results in the selective delivery of energy to only the surface tissues, the applicator comprising multiple positive and negative electrodes provided in an alternating arrangement in the applicator. Two possible examples of suitable alternating positive and negative electrode arrangements are a matrix (chess-board) arrangement of alternating positive and negative electrodes or a concentric ring arrangement of alternating positive and negative electrodes. The arrangement can be used with or without a conventional bolus and does not require the use of an opposed counter electrode.

Or further alternatively, the applicator electrode can be a flexible non-bolus type electrode. The flexible electrode can be in the form of a belt or bandage with lightning fastener. For example it could be a belt-like shape having paired electrodes, for example, with one pair or two pairs of capacitive electrodes. Instead of a coated flexible carrier or a coated flexible material a conductive metallic net or a conductive metallic network can be used, manufactured of at least one conductive metal electrode material. Such metallic nets or metallic networks preferably do not comprise any backbone such as a polymeric network structure. The metallic net or network is preferably a woven structure of metallic fibres having very similar properties as the coated flexible material such as a coated textile. The conductive metallic net or network is flexible, allows water and other fluids as well as gases to move through, can be folded without negative effect concerning conductivity and is able to cover uneven, fractal and/or percolative surfaces. Consequently, all kind of metallic nets and networks having the afore-mentioned properties of the conductively coated materials such as the conductively coated textiles are useful within the inventive electromagnetic energy transfer means. The conductive metal coating is a multilayer coating. Preferably, one of the layers is silver which has a good antibacterial effect and provides for good radiofrequency (RF) conductivity. Moreover, silver has an anti-odour effect together with moderate anti-perspiration activity. Therefore silver is preferred for cosmetic, medical and well-being applications. However, other conductive metal coatings can be used also. The resulting conductive metal coated flexible material is still sufficiently porous to allow for the exchange of heat and fluids.

Another aspect of the present invention is the use of the inventive radiofrequency (RF) hyperthermia device to provide an improved method for selectively treating a localised target site. The inventive hyperthermia device is especially useful for the treatment of pain, cancer, solid tumors but also cancer metastases.

Thus, the hyperthermia device of the present invention can be used to selectively treat a localised target site wherein the localised target site is selected from tumour tissues and muscle tissue, or organs, such as for example liver, lung, heart, kidney, spleen, brain, ovary, uterus, prostate, pancreas, larynx, the gastrointestinal tract, and the gynaecological tract.

The tumour tissue can be selected from adenocarcinoma, choroidal melanoma, acute leukemia, acoustic neurinoma, ampullary carcinoma, anal carcinoma, astrocytoma, basal cell carcinoma, pancreatic cancer, desmoid tumour, bladder cancer, bronchial carcinoma, non-small cell lung cancer (NSCLC), breast cancer, Burkitt's lymphoma, corpus cancer, CUP-syndrome (carcinoma of unknown primary), colorectal cancer, small intestine cancer, small intestinal tumours, ovarian cancer, endometrial carcinoma, ependymoma, epithelial cancer types, Ewing's tumours, gastrointestinal tumours, gastric cancer, gallbladder cancer, gall bladder carcinomas, uterine cancer, cervical cancer, cervix, glioblastomas, gynecologic tumours, ear, nose and throat tumours, hematologic neoplasias, hairy cell leukemia, urethral cancer, skin cancer, skin testis cancer, brain tumours (gliomas), brain metastases, testicle cancer, hypophysis tumour, carcinoids, Kaposi's sarcoma, laryngeal cancer, germ cell tumour, bone cancer, colorectal carcinoma, head and neck tumours (tumours of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's), lymphomas, stomach cancer, malignant melanoma, malignant neoplasia, malignant tumours gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, squamous cell carcinoma of the head and neck (SCCHN), prostate cancer, pharyngeal cancer, rectal carcinoma, retinoblastoma, vaginal cancer, thyroid carcinoma, Schneeberger disease, esophageal cancer, spinalioms, T-cell lymphoma (mycosis fungoides), thymoma, tube carcinoma, eye tumours, urethral cancer, urologic tumours, urothelial carcinoma, vulva cancer, wart appearance, soft tissue tumours, soft tissue sarcoma, Wilm's tumour, cervical carcinoma and tongue cancer. Particularly suitable for treatment are, for example, astrocytomas, glioblastomas, pancreatic cancer, bronchial cancer, breast cancer, colorectal cancer, ovarian cancer, gastric cancer, laryngeal cancer, malignant melanoma, oesophageal cancer, cervical cancer, liver cancer, bladder cancer, and renal cell cancer The hyperthermia device of the present invention can be used in combination with chemotherapy treatment with cytostatic and/or cytotoxic drugs. Example of some cytostatic and/or cytotoxic drugs are actinomycin D, aminoglutethimide, amsacrin, anastrozol, antagonists of purine and pyrimidine bases, anthracycline, aromatase inhibitors, asparaginase, antiestrogenes, bexaroten, bleomycin, buselerin, busulfan, camptothecin derivates, capecitabin, carboplatin, carmustine, chlorambucil, cisplatin, cladribin, cyclophosphamide, cytarabin, cytosinarabinoside, alkylating cytostatics, dacarbacin, dactinomycin, daunorubicin, docetaxel, doxorubicin (adriamycin), doxorubicin lipo, epirubicin, estramustine, etoposid, exemestan, fludarabin, fluorouracil, folic acid antagonists, formestan, gemcitabin, glucocorticoides, goselerin, hormones and hormone antagonists, hycamtin, hydroxy urea, idarubicin, ifosfamid, imatinib, irinotecan, letrozol, leuprorelin, lomustin, melphalan, mercaptopurine, methotrexate, miltefosin, mitomycine, mitosis inhibitors, mitoxantron, nimustine, oxaliplatin, paclitaxel, pentostatin, procarbacin, tamoxifen, temozolomid, teniposid, testolacton, thiotepa, thioguanine, topoisomerase inhibitors, topotecan, treosulfan, tretinoin, triptorelin, trofosfamide, vinblastine, vincristine, vindesine, vinorelbine, antibiotics with cytotoxic activities. All present and future cytostatics or other medicaments including gene therapy could be applied.

When used for treatment of inflammatory conditions the hyperthermia device of the present invention can be used in combination with an anti-inflammatory drug treatment such as a non-steroidal anti-inflammatory drug (NSAID), for example, alcofenac, aceclofenac, sulindac, tolmetin, etodolac, fenopren, thiaprofenic acid, meclofenamic acid, meloxicam, tenoxicam, lornoxicam, nabumetone, acetaminophen, phenacetin, ethenzamide, sulpyrine, mefanamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesilate, camostat mesilate, ulinastatin, colchicine, probenecid, sulfinpyrazone, benzbromarone, allopurinol, salicylic acid, atropine, scopolamine, levorphanol, ketorolac, tebufelone, tenidap, clofezone, oxyphenbutazone, prexazone, apazone, benzydamine, bucolome, cinchopen, clonixin, ditrazol, epirizole, fenoprofen, floctafenin, glaphenine, indoprofen, niflumic acid and suprofen, or with a steroidal anti-inflammatory drugs, for example, dexamethasone, hexestrol, methimazole, betamethasone, triamcinolone, fluocinonide, prednisolone, methylprednisolone, hydrocortisone, fluorometholone, beclomethasone dipropionate, estriol, clobetasol, diflorasone diacetate, halbetosal propionate, amicinonide, desoximetasone, halcinonide, mometasone furoate, fluticasone propionate, flurandrenolide, clocortalone, predincarbate, aclometasone dipropionate and desonide.

Another aspect of the present invention is the use of the inventive hyperthermia device to provide an improved method of hyperthermia treatment for upper respiratory tract disease. Upper respiratory tract infections are caused by viruses and bacteria that have an optimum growth and survival temperature lower than the core body temperature. Therefore these infections can also be treated using hyperthermia therapy. For example, in bacterial infections of the upper part of the respiratory system (e.g. a common cold) the positive effect of heat application is well-known. The mucosa is highly conductive. Similar as in tumor tissue the heat effect is also concentrated (as in asthma treatment). Consequently, the inventive method is higher selective for a common cold than other heating techniques. Thus the hyperthermia device of the present invention is also useful for the treatment of rhinitis and other upper respiratory tract infections. Examples of viruses that cause upper respiratory tract infections are rhinoviruses, coronaviruses, adenoviruses, myxoviruses, coxsackie viruses, echoviruses, parainfluenza viruses, respiratory syncytial virus and influenza viruses. Examples of bacteria that cause upper respiratory tract infections are *Mycoplasma pneumoniae, Chlamydia pneumoniae, Streptococcus pneumoniae, Corynebacterium diptheriae,* and *Haemophilus influenzae.*

Another aspect of the present invention is the use of the inventive hyperthermia device to provide an improved method of hyperthermia treatment for pain management, In these cases the treatment could be carried out at normal body temperature or at least so that the temperature increase in the target tissue is negligible.

Another aspect of the present invention is a method for modulating a signal of a radiofrequency device comprising a radiofrequency source (1) which provides a source signal (8) an amplifier (2), a sensor (3), a feed back amplifier (6) and a modulation signal generator (13), comprising the steps of:

modulating the source signal (8) with a signal from the modulation signal generator to generate a modulated source signal (10), amplifying the modulated source signal (10) with the amplifier, directing the signal to a target (17), receiving a feedback signal (5) from the target at the sensor, directing the feedback signal to the feed back amplifier, amplifying the feedback signal with the feedback amplifier, the feedback signal modulating the signal from the modulation signal generator (13), and modulating the source signal with the modulated signal from the modulation signal generator to generate a modulated source signal (4).

EXAMPLES

Example 1

Figure 26A:
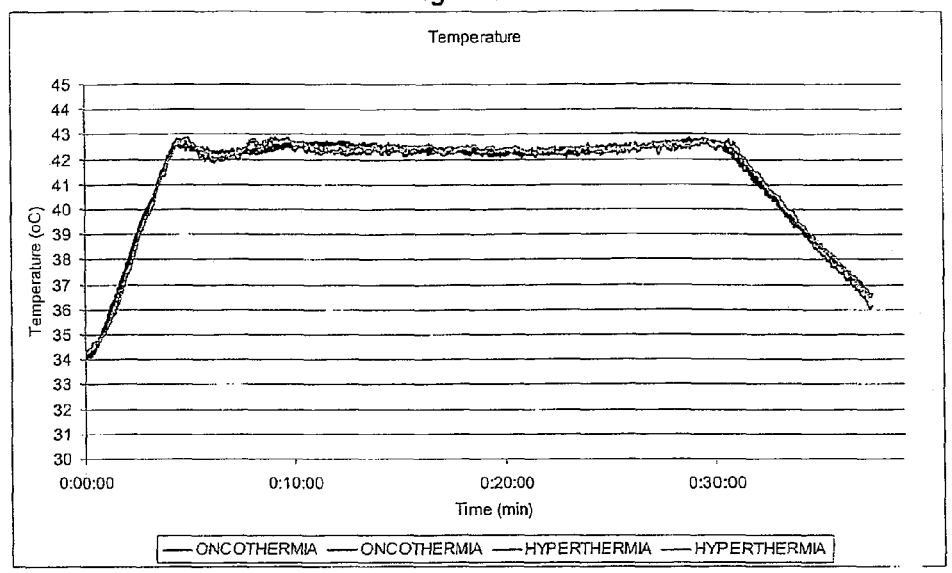
FIGS. 26 (A and B) show the macroscopic temperature measurement (Luxtron sensor, FIG. 26A) and the microscopic (subcellular Luciferase activity, FIG. 26B) temperature comparison of the hyperthermia and oncothermia measurements in Luc-GFP transient transfected HEK293 cell line.
Figure 26B:
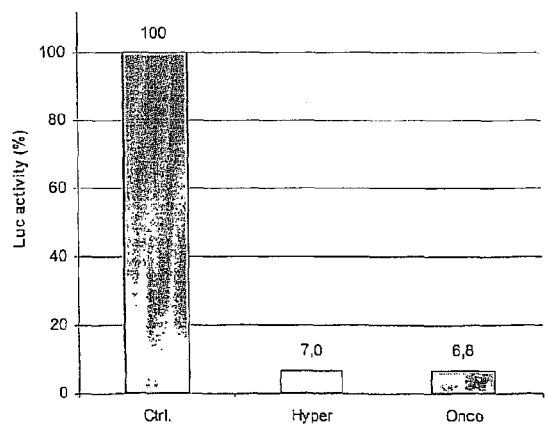

A co-culture of normal human skin fibroblasts and aggressive A431 squamous cell carcinoma cells (a malignant melanoma cell line) as a model of a squamous carcinoma growing within connective tissue cells were treated with the device of the present invention (labelled oncothermia) for 30 minutes at 42° C. Temperature was exactly determined by means of Luxtron flouroptical sensors having no metallic components near the sample. Due to the importance of temperature as control of standardized treatment the macroscopic temperature should be equal to the microscopic temperature. The microscopic (subcellular) temperature was verified by transfected Luciferase (as a molecular thermometer). The model used The cell-line HEK293 was used as a model. Luciferase was co-transfected with non-temperature-sensitive GFP as reference. Macrosciopic and microscopic temperature measurements are shown in FIGS. 26A and 26B. The identity is compelling.

Figure 8:
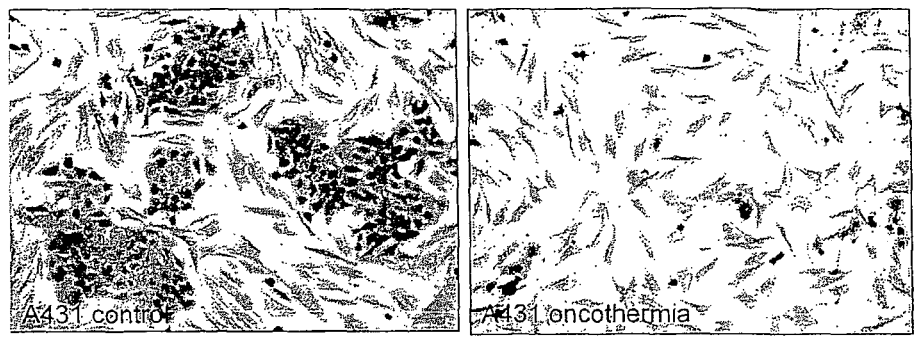
FIG. 8 shows a co-culture of normal human skin fibroblasts and aggressive A431 squamous cell carcinoma cells (a malignant melanoma cell line) treated with the device of the present invention (labelled oncothermia)

All comparison studies were carefully managed in their dynamics as well. Not only the temperature was kept constant in the samples, but also the heating and cooling dynamics were controlled and kept equivalent so the heating and cooling slopes kept strictly identical also (see FIG. 26A). Subsequently the culture was incubated for 24 h at 37° C., fixed and stained with crystal violet. Selectivity at the cellular level was observable after treatment. The malignant cells have been destroyed but the healthy fibroblasts remain intact as shown in FIG. 8.

Example 2

Figure 9:
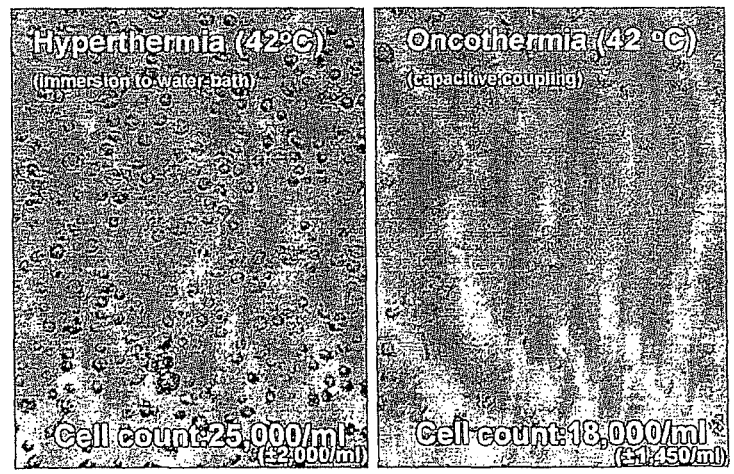
FIG. 9 shows a HL60 human acute promyelocytic leukaemia cell-line treated with the device of the present invention.

The same selectivity was demonstrated in the HL60 leukaemia cell-line (Human acute promyelocytic leukaemia cell line in cell suspension culture, RPMI-1640, 10% FBS). A culture of HL60 leukaemia cells was treated with the device of the present invention (labelled oncothermia) for 30 minutes at 42° C. see above in comparison to HL60 leukaemia cells treated with a conventional hyperthermia device (labelled hyperthermia) for 30 minutes at 42° C. see above. The heating of the cells is identical in comparison of the conventional device and the inventive device. However, the result achieved by the inventive device (cell count: 18,000 cells/ml after treatment) is significantly improved in comparison to the conventional device (cell count: 25,000 cells/ml after treatment) as shown in FIG. 9.

Example 3

Figure 10:
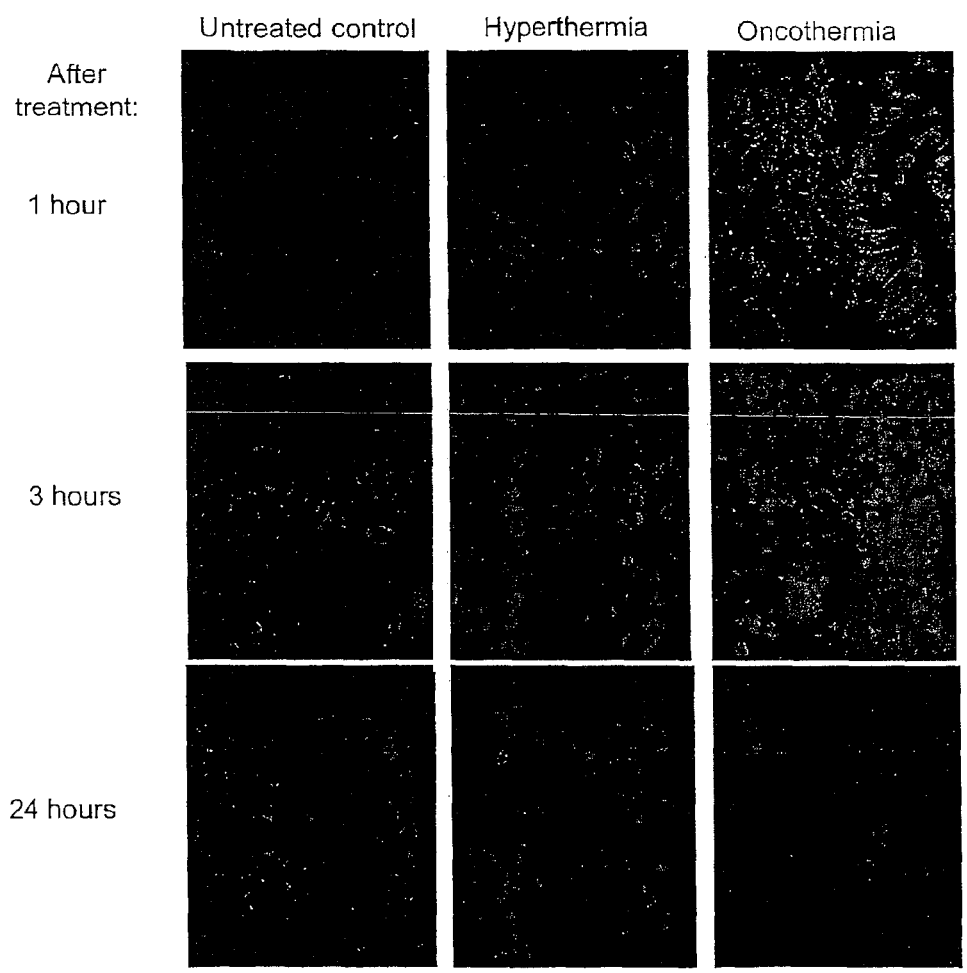
FIG. 10 shows a co-culture of human healthy fibroblasts and A431 squamous carcinoma cells treated with device of the present invention (labelled oncothermia) in comparison to cells treated with a conventional hyperthermia device (labelled hyperthermia)

A co-culture of human healthy fibroblasts and A431 squamous carcinoma cells growing in normal human skin fibroblasts cells (100,000/ml) was treated with the device of the present invention (labelled oncothermia) for 30 minutes at 42° C. see above in comparison to the same cells treated with a conventional hyperthermia device (labelled hyperthermia) for 30 minutes at 42° C. see above. Subsequently the culture was incubated for 24 h at 37° C. Success was measured by beta catenin development over time after the treatment as shown in FIG. 10.

Example 4

An apoptosis/necrosis experiment was performed on a HT29 human colorectal carcinoma tumour xenograft model in nude mice. The mice were treated using the inventive device for 30 minutes at 42° C. see above in comparison to a conventional hyperthermia device for 30 minutes at 42° C. see above. Using Roche's in situ cell death detection kit, DAPI staining was performed (staining only the double strands of DNA) and Tunel-FIC (enzymatically labelling the strand-break of DNA). The observed cell-death when treated with a conventional hyperthermia device was mainly necrotic, while the observed cell-death when treated with the inventive hyperthermia device was mainly apoptotic.

Example 5

Treatment of pain was performed on 48 patients suffering from glioma (12 patients), rheumatic pain (17 patients), migraine (10 patients), joint-pains (9 patients). The treatment was performed by an electrode having 30 cm diameter for treatment of chest, 10 cm diameter for the treatment of the head and 7 cm diameter for the treatment of the knees, placed on the chest, the back, head or knee of the patient. The treatment was provided three times a week (every second day) during a month, and before and after each treatment the patients were asked to assess their degree of pain according to a chart from 1 to 10 wherein 1 means no pain and 10 stand for incredible pain. The applied power was 150 W for 1.5 hours, in step-up process (starting from 80 W, and increasing the power till 150 W by 5 min intervals with 20 W (last is 10 W). The full provided energy was about 780 kJ.

Figure 27:
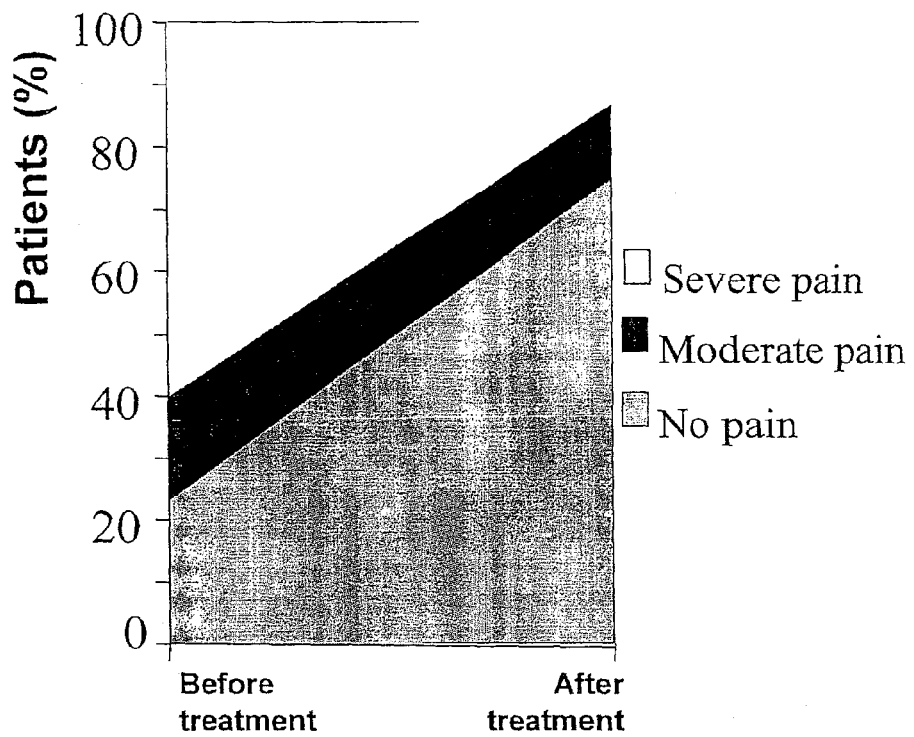
FIG. 27 Shows the improvement in pain reduction during hyperthermia treatment. The degree of pain was subjectively assessed by the patients before and after hyperthermia treatment by 48 patients.

The result of the pain treatments is shown in FIG. 27. The very advantageous result was that one third of all patients with severe pain (score between 7-10) before the hyperthermia treatment stated to be pain free after the treatment.

Example 6

The effect of our treatment on patients with obstructive respiratory diseases was carried out on a limited number of patients, to provide a treatment for acute or chronic allergic rhinitis, asthma, infectious diseases of upper respiratory tract.

The total number of enrolled and evaluated patients was 19, the patients were divided into 3 groups:

patients with chronic obstructive bronchitis (5 patients)

asthma bronchialis (III.-IV. grade, for more than 10 years) (11 patients)

asthma bronchiale (I.-II. grade for not more than 2 years) (3 patients)

The baseline status and the progress status of the patients were measured by respiratory function tests, peak-flow meter testing (twice a day) and questionnaire about subjective status of the patients (according to accepted standard)+patients' diary during the treatment).

The treatment was performed by the electrode 30 cm diameter, placed on the chest of the patient. The treatment was provided three times a week (every second day) during a month, and after it was a follow-up period. The applied power was 150 W for 1.5 hours, in step-up process (starting from 80 W, and increasing the power till 150 W by 5 min intervals with 20 W (last is 10 W). The full provided energy was 774.6 kJ.

We came to the conclusion that the hyperthermia treatment using the inventive device has advantageous effects on the treated patients in that their lung-function parameters became better and their subjective feeling was significantly better.

We measured the Peak Expiratory Flow-rate (PEF) and the Forced Expiratory Volume in $1^{st}$ second, (FEV1) [Spirometry]. The most promising indications came from the Asthma bronchiale (III.-IV. grade) patient group with severe and serious symptoms, where in case of 7 patients the PEF value increased by more than 25%. Out of the 11 patients 10 declared their general subjective status as definitively better, only 1 patient indicated worse subjective status.

Two case reports:
Patient: female, 57 years old
Status: Asthma bronchiale diagnosed in 1996, stage
Applied therapy:
Serevent rotadisk
Pulmicort 400 µg turbuhaler
Ventolin spay
Results:

|  | Date | | | | | | |
|---|---|---|---|---|---|---|---|
| Meas. | 04.09.2000. | 03.10.2000. | 21.03.2001. | 02.05.2001. | 06.06.2001. | 05.07.2001. | 07.08.2001. |
| FEV 1 [l] | 1.92 | 2.12 | 1.94 | 2.01 | 1.97 | 1.9 | 1.7 |
| PEF [l/s] | 3.58 | 7.17 | 5.36 | 6.61 | 5.6 | 5.77 | 4.28 |
|  |  |  |  | Only Ventolin therapy is applied | | | |

Figure 11:
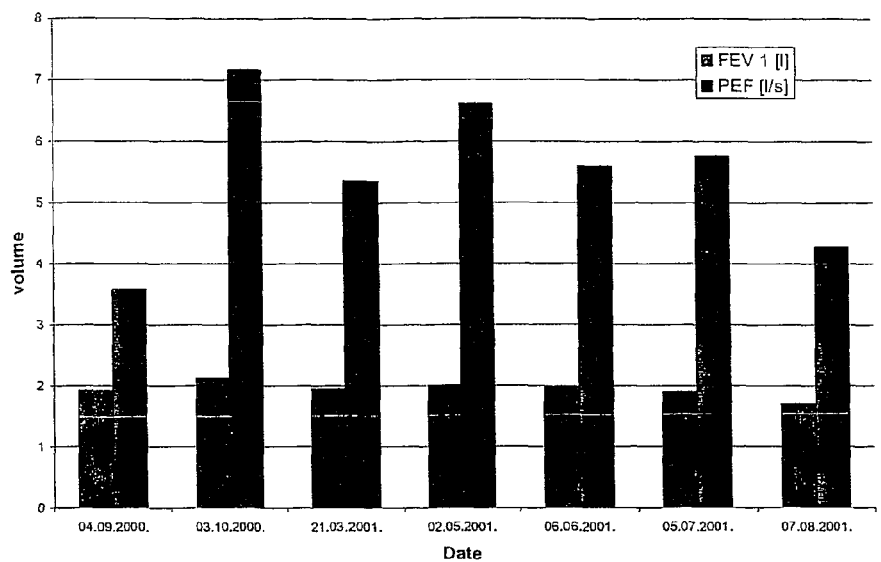
FIG. 11 shows the measured Peak Expiratory Flow-rate (PEF in L/s) and the Forced Expiratory Volume in $1^{st}$ second, (FEV1 in L) [Spirometry] at 7 dates.

The results are shown in FIG. 11.
Summary of the results:
After the third treatment a considerable cough void, at first yellowish, later white,
Increased general status of the patient,
Increased patient's efficiency,
Previous drug doses were reduced, later only Ventolin was applied,
Uses bronchiole-dilator only on rare occasions,
The improvement looks permanent.
Two case reports:
Patient: female, 55 years old
Status: Asthma bronchiale intr. diagnosed in 1993, stage IV:
Patient suffered from:
diabetes mellitus,
osteoporosis,
hypertension.
Applied therapy: (additional to the diabetes mellitus, hypertension and osteoporosis):
Pulmicort 400 µg turbuhaler,
Theospirex 300 mg,
Medrol 8 mg/day,
Berodual inhalation solution plus spray.
Results:

|  | Date | | | |
|---|---|---|---|---|
| Meas. | 10.10.2000. | 20.11.2000. | 13.03.2001. | 25.07.2001. |
| FEV 1 [l] | 0.98 | 1.42 | 1.36 | 1.15 |
| PEF [l/s] | 2.06 | 3.66 | 3.00 | 2.91 |
|  | Steroid treatment is terminated, Only retain pulmicor is applied. | | | |

Figure 12:
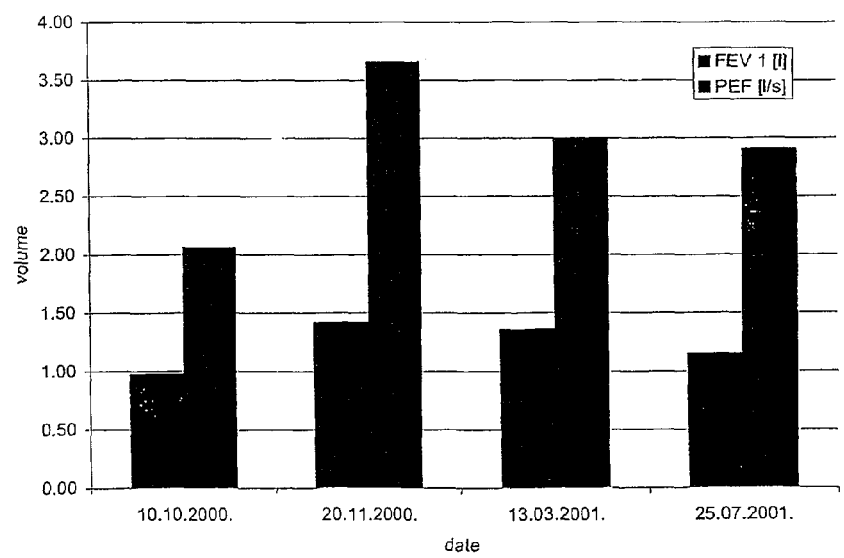
FIG. 12 shows the measured Peak Expiratory Flow-rate (PEF in L/s) and the Forced Expiratory Volume in $1^{st}$ second, (FEV1 in L) [Spirometry] at 4 dates.

The results are shown in FIG. 12.
Summary of the results:
Out of seven patients breath-function was increased in five, unchanged in 2, minimally 22% significant changes on the patient status, (the highest change was a triple of the initial). In the two "no-change" patients acut catarrhal exacerbatio.

Conclusion of the pulmonary track non-oncologiocal cases and treatments:
After the third treatment a considerable cough void, at first yellowish, later white,
Breathlessness decreased or terminated,
Bronchial obstruction demolished, bronchial mucosity passes,
Increased general status of the patient,
Increased patient's efficiency,
Previous drug doses were reduced, later only ventolin was applied,
Uses bronchiole-dilator only on rare occasions,
The improvement looks permanent,
The treatment is well tolerable, no side effects were observed.

The invention claimed is:

1. A radiofrequency hyperthermia device for capacitive coupling, without a dipole antenna, comprising:
  a radiofrequency source;
  an amplifier;
  a sensor configured for detecting a reflected or transmitted power signal from a target tissue;
  a pink noise generator;
  a modulator which effects changes in amplitude of an output of the radiofrequency source based on an output of the pink noise generator;
  at least one electrode; and
  at least one counter-electrode;
  wherein the radiofrequency source is configured to produce a carrier wave having a carrier frequency, the pink noise generator is configured to produce an information signal, and the modulator is configured to modulate the amplitude of the carrier wave based on the information signal produced by the pink noise generator through amplitude modulation to generate a modulated carrier wave signal;
  wherein the amplifier is configured to amplify the modulated carrier wave signal and to direct the modulated carrier wave signal to the target tissue through the at least one electrode and at least one counter-electrode;
  wherein the sensor is configured to receive a feedback signal from the target tissue, and the feedback signal is configured to provide feedback correction to the information signal provided by the pink noise generator through a multiplicator to generate a target modified modulated signal; and
  wherein the radiofrequency hyperthermia device is configured to generate an electric field between the electrode and the counter-electrode and use capacitive coupling to apply a RF current through the target tissue.

2. The radiofrequency device of claim 1, further comprising a feedback amplifier for amplifying the feedback signal.

3. The radiofrequency device of claim 1, wherein the feedback signal modulates the modulation signal from the modulation signal generator.

4. The radiofrequency device of claim 1, wherein the carrier wave is modulated by the information signal from the pink noise generator that has been modulated by the feedback signal.

5. The radiofrequency device of claim 1, wherein the sensor is situated between the amplifier and the target.

6. The radiofrequency device of claim 1, wherein the sensor is situated between the target and a feedback amplifier.

7. The radiofrequency device of claim 1, wherein the amplitude and frequency spectrum of the carrier wave is modulated.

8. A method of hyperthermia treatment in a subject comprising:
   applying an RF current to a subject using a radiofrequency device for capacitive coupling, without a dipole antenna, the radiofrequency device comprising:
   a radiofrequency source;
   an amplifier;
   a sensor configured for detecting a reflected or transmitted power signal from a target tissue;
   a pink noise generator;
   a modulator which effects the changes in amplitude of an output of the radiofrequency source based on an output of the pink noise generator;
   at least one electrode and at least one counter electrode;
   wherein the radiofrequency source produces a carrier wave whose amplitude is modulated by the modulator and an information signal produced by the pink noise generator through amplitude modulation to generate a modulated carrier wave signal, wherein the modulated carrier wave signal is amplified by the amplifier and directed to a target tissue through the at least one electrode and at least one counter-electrode, and the sensor receives a feedback signal from the target tissue;
   wherein the feedback signal provides feedback correction to the information signal produced by the pink noise generator through a multiplicator to generate a target modified modulated signal; and
   wherein the radiofrequency hyperthermia device generates an electric field between the electrode and the counter-electrode and uses capacitive coupling to apply the RF current through the target tissue.

9. The method of claim 8, wherein the radiofrequency device further comprises a feedback amplifier for amplifying the feedback signal.

10. The method of claim 8, wherein the hyperthermia treatment is used for the prophylaxis, treatment and after-treatment of tumours, cancer, metastases, carcinomas, pain, migraine and diseases of the central nervous system.

11. A method for modulating a signal of a radiofrequency device, the radiofrequency device comprising:
    a radiofrequency source which provides a carrier wave;
    an amplifier;
    a sensor configured for detecting a reflected or transmitted power signal from a target tissue;
    a feedback amplifier;
    a pink noise generator;
    a modulator which effects changes in amplitude to the carrier wave;
    at least one electrode; and
    at least one counter electrode;
    the method comprising the steps of:
    modulating the carrier wave with an information signal from the pink noise generator to generate a modulated carrier wave through amplitude modulation;
    amplifying the modulated carrier wave with the amplifier;
    directing the modulated carrier wave to the target tissue;
    generating an electric field between the electrode and the counter-electrode;
    applying a RF current through the target tissue;
    receiving a feedback signal representing reflected or transmitted power from the target at the sensor;
    directing the feedback signal to the feedback amplifier;
    amplifying the feedback signal with the feedback amplifier, the feedback signal modulating the information signal from the pink noise generator through a multiplicator; and
    modulating the source signal with the modulated information signal from the pink noise generator to generate a modulated source signal.

* * * * *